US008094294B2

(12) United States Patent
Treado et al.

(10) Patent No.: US 8,094,294 B2
(45) Date of Patent: Jan. 10, 2012

(54) MULTIPOINT METHOD FOR IDENTIFYING HAZARDOUS AGENTS

(75) Inventors: Patrick J Treado, Pittsburgh, PA (US); Joseph E Demuth, Naples, FL (US); Robert Schweitzer, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 242 days.

(21) Appl. No.: 12/422,360

(22) Filed: Apr. 13, 2009

(65) Prior Publication Data

US 2011/0299071 A1 Dec. 8, 2011

Related U.S. Application Data

(63) Continuation of application No. 11/000,683, filed on Nov. 30, 2004, now Pat. No. 7,538,869.

(60) Provisional application No. 60/591,132, filed on Jul. 26, 2004, provisional application No. 60/584,718, filed on Jun. 30, 2004.

(51) Int. Cl.
*G01N 21/35* (2006.01)
*G01N 21/64* (2006.01)
*G01N 21/65* (2006.01)

(52) U.S. Cl. .......... 356/73; 356/301; 356/317; 356/326; 356/417; 356/451; 250/339.07

(58) Field of Classification Search ........................ None
See application file for complete search history.

(56) References Cited

U.S. PATENT DOCUMENTS

| | | | |
|---|---|---|---|
| 4,784,486 | A | 11/1988 | Van Wagenen |
| 4,880,052 | A | 11/1989 | Meyer |
| 5,194,912 | A | 3/1993 | Batchelder |
| 5,377,004 | A | 12/1994 | Owen |
| 5,442,438 | A | 8/1995 | Batchelder |
| 5,528,393 | A | 6/1996 | Sharp |
| 5,539,517 | A | 7/1996 | Cabib |
| 5,623,342 | A | 4/1997 | Baldwin |
| 5,689,333 | A | 11/1997 | Batchelder |
| 5,710,626 | A | 1/1998 | O'Rourke |
| 5,818,047 | A | 10/1998 | Chaney |
| 5,828,450 | A | 10/1998 | Dou |
| 5,862,273 | A | 1/1999 | Pelletier |
| 5,866,430 | A | 2/1999 | Grow |
| 5,901,261 | A | 5/1999 | Wach |
| 5,911,017 | A | 6/1999 | Wach |
| 6,002,476 | A | 12/1999 | Treado |
| RE36,529 | E | 1/2000 | Lewis |

(Continued)

FOREIGN PATENT DOCUMENTS

JP 9121889 5/1997

OTHER PUBLICATIONS

Caetano et al, "Evaluation of the Importance of Non-Linear Spectra Mixing in Coniferous Forests," SPIE vol. 3499. Sep. 1998, pp. 257-269.

(Continued)

*Primary Examiner* — F. L. Evans

(57) ABSTRACT

The invention relates to apparatus and methods for assessing occurrence of a hazardous agent in a sample by performing multipoint spectral analysis of the sample. Methods of employing Raman spectroscopy and other spectrophotometric methods are disclosed. Devices and systems suitable for performing such multipoint methods are also disclosed.

32 Claims, 22 Drawing Sheets
(6 of 22 Drawing Sheet(s) Filed in Color)

U.S. PATENT DOCUMENTS

| | | | |
|---|---|---|---|
| 6,081,612 | A | 6/2000 | Gutkowicz-Krusin |
| 6,316,772 | B1 | 11/2001 | Egeleberg |
| 6,717,668 | B2 | 4/2004 | Treado |
| 6,734,962 | B2 | 5/2004 | Treado |
| 6,765,668 | B2 | 7/2004 | Gardner |
| 6,788,407 | B1 | 9/2004 | Higdon |
| 6,917,423 | B2 | 7/2005 | Gardner |
| 6,954,667 | B2 | 10/2005 | Treado |
| 6,965,793 | B2 | 11/2005 | Treado |
| 7,538,869 | B2 * | 5/2009 | Treado et al. ................. 356/301 |
| 2005/0185178 | A1 | 8/2005 | Gardner |
| 2006/0019409 | A1 | 1/2006 | Nelson |
| 2006/0268266 | A1 | 11/2006 | Gardner |

OTHER PUBLICATIONS

Rasmussen et al, "Liberty Retrieval of Infrared Spectra Based on Detailed Intensity Information," Applied Spectroscopy, vol. 33, No. 4, 1979, pp. 371-376.

Guilment et al., "Infrared Chemical Micro-Imaging Assisted by Interactive Self-Modeling Multivariate Analysis," Applied Spectroscopy, vol. 48, No. 3 1994, pp. 320-326.

Grow et al., "New Biochip Technology for Label-Free Detection of Pathogens and their Toxins," Journal of Microbiological Methods, vol. 53, 2003, pp. 221-233.

* cited by examiner

MULTIPOINT METHOD FOR IDENTIFYING HAZARDOUS AGENTS

CROSS-REFERENCES TO RELATED APPLICATIONS

This application is a continuation of U.S. patent application Ser. No. 11/000,683, entitled "Multipoint Method for Identifying Hazardous Agents", which was filed on 30 Nov. 2004 now U.S. Pat. No. 7,538,869 and is entitled to priority pursuant to 35 U.S.C. §119(e) to U.S. provisional patent application 60/584,718, which was filed on 30 Jun. 2004 and to U.S. provisional patent application 60/591,132, which was filed on 26 Jul. 2004.

BACKGROUND OF THE INVENTION

The invention relates generally to the field of Raman spectroscopy.

Deliberate and inadvertent deployments of harmful or weaponized chemical or biological agents pose significant threats to public welfare, as do explosives and radiological materials. Such agents threaten both human and economic health, and the threats posed by these agents are compounded by limited ability to detect deployment of the agents and to respond appropriately.

The mass destruction potential of biological weapon agents (BWAs) and chemical weapon agents (CWAs) is considered comparable to or even greater than that of nuclear weapons. Nuclear weapons have the potential to affect a finite area, albeit very large, and the use of such weapons is immediately obvious after the fact. The geographical site and boundaries of attacks using BWAs and CWAs are not readily apparent, and can be difficult to identify in a period of time relevant to permit effective response. Once unleashed, these agents can spread silently and unchecked through populations far from ground zero. Technology to rapidly detect and quantify radiation, even at very low levels, is widely available. Unfortunately, such technology for BWAs and CWAs at similar levels is not definitive, not widely available and in many cases, is not very rapid. A significant need exists for apparatus and methods useful for detecting and quantifying BWAs and CWAs in a timely manner.

Conventional means of identifying biological pathogens include methods and reagents such as specific antibodies, genetic markers, and propagation in culture. Most of these methods are slow, labor-intensive, and dependent on detection of highly-specific molecular structures. Using modern biotechnology methods, it is possible to alter many human pathogens in ways that can limit traditional detection methods, increase their pathogenicity, increase their resistance to conventional therapy, or some combination of these. Engineered BWAs pose a greater threat as biotechnology information becomes more widely available. Conventional tools for detecting BWAs are likely to become less effective over time as such knowledge spreads.

As unintended or deliberate use of BWAs and CWAs becomes a greater threat, there is an increased need for tools that can rapidly and accurately detect and classify these agents at a molecular level, preferably without coming into contact with them. These tools are also needed to help expand our understanding of the biological and chemical nature of such agents and their potential impact on the human body. The present invention satisfies these needs.

BRIEF SUMMARY OF THE INVENTION

The invention relates to a method of assessing occurrence of a hazardous agent in a sample. The method comprises irradiating the sample with light and assessing Raman-shifted scattered radiation emanating from multiple points in the sample. The multiple points have a defined geometric relationship. The Raman-shifted scattered radiation is characteristic of the presence or absence of the hazardous agent in the sample. For example, Raman-shifted scattered radiation emanating from three, six, or ten points can be assessed. The points in the sample can be colinear, lie along two intersecting lines, be radially equidistant from a central point, or arranged otherwise, such as a random distribution not determinable from an image.

The methods described herein can significantly speed Raman scattering analysis of a sample, because the points at which Raman scattering is assessed need not represent more than 25% of the area of the field of view, and can represent 5%, 1%, or less of the field.

The methods described herein are useful for assessing occurrence of a wide variety of hazardous agents. Examples of such hazardous agents include biological toxins, microorganisms (e.g., bacteria and protozoa), viruses, and chemical agents.

Raman-shifted scattered radiation can be transmitted through a spectrometer, a filter, or an interferometer prior to assessing the Raman-shifted scattered radiation for the presence or absence of the hazardous agent. The method can be performed using a variety of Raman-shifted scattered radiation collection systems. Such systems can be based on devices such as macroscopes, microscopes, endoscopes, telescopes, and fiber optic arrays.

The methods described herein can also be used to identify a hazardous agent in a sample or (if the agent is a biological agent) to assess its viability. The invention includes devices and systems for performing such methods.

BRIEF SUMMARY OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 4 consists of FIGS. 4A and 4B.

FIG. 7, consisting of FIGS. 7A and 7B, depicts fluorescence multipoint spectral differentiation and identification of different *Bacillus* species in a mixture of *B. pumilus* and *B. subtilis*.

FIG. 8, consisting of FIGS. 8A, 8B, 8C, and 8D, depicts Raman multipoint identification of the *B. anthraces* simulant *B. globigii* in a mixture of white powders (baking soda and SWEET-N-LOW® brand saccharine sweetener).

FIG. 10, consisting of FIGS. 10A, 10B, 10C, and 10D, depicts use of NIR multipoint spectral sensing can be used to detect and identify objects (aspirin, lactose, and *Bacillus thurigiensis*) in sealed envelops and containers.

DETAILED DESCRIPTION OF THE INVENTION

Figure 1:
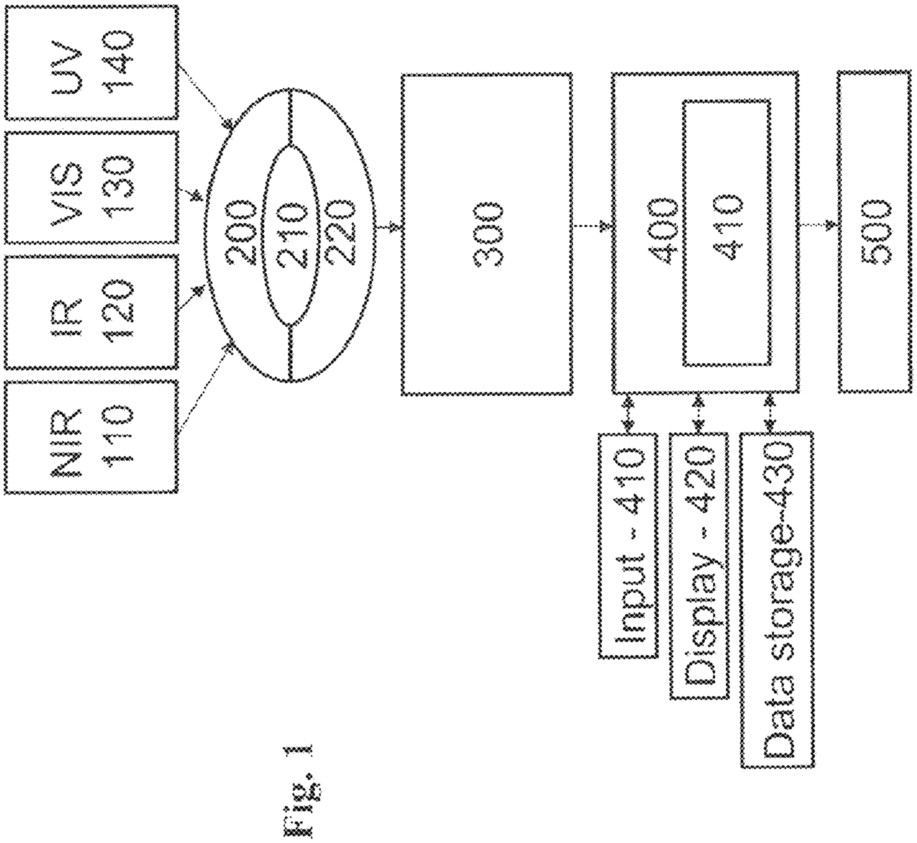
FIG. 1 is a schematic diagram of a Raman spectroscopy instrument suitable for use in the multipoint sensing and detection systems described herein.

The invention relates to a method of assessing occurrence of a hazardous agent in a sample. The method comprises irradiating the sample with light and assessing Raman-shifted scattered radiation emanating from multiple points in the sample. The points having a defined (e.g., predetermined or known) geometric relationship. By assessing the Raman-shifted scattered radiation emitted from the points for the presence or absence of Raman spectral properties that are characteristic of the hazardous agent, the presence or absence of the hazardous agent in the sample can be determined. An important aspect of the invention is the discovery that the presence or absence of a hazardous agent in a sample can be estimated accurately by assessing Raman scattering from multiple points in the sample. Sampling of multiple points in a relatively large field of view can yield compositional information about the sample in the field without the need either to collect extensive data from all points in the field or to average the spectral information of the entire field. The multipoint imaging methods described herein can therefore be used to determine both the composition of a sample and the degree of homogeneity within the sample.

DEFINITIONS

As used herein, each of the following terms has the meaning associated with it in this section.

"Bandwidth" means the range of wavelengths in a beam of radiation, consistent with a specified full width at half maximum.

"Bandpass" of a detector or other system means the range of wavelengths that the detector or system can distinguish, as assessed using the full width at half maximum intensity method.

The "full width at half maximum" ("FWHM") method is a way of characterizing radiation including a range of wavelengths by identifying the range of contiguous wavelengths that over which the magnitude of a property (e.g., intensity or detection capacity) is equal to at least half the maximum magnitude of that property in the radiation at a single wavelength.

A "hazardous agent" is a substance (e.g., a chemical, biological, radiological, or explosive material) that can cause disease, injury, discomfort, pain, or death to an animal such as a human.

A "point" in a sample refers to a relatively small area of an illuminated field including at least part of a sample. For example, in a circular microscopic field, points can represent less than 100% (e.g., 20%, 10%, 5%, 1%, or less) of the illuminated microscopic field. The geometry of the area corresponding to a point is not critical. For example, a point can refer to a circular, annular, or square area of a sample.

The terms "optical" and "spectroscopic" are used interchangeably herein to refer to properties of materials (and to methods of assessing such properties). The term "spectroscopic" is generally understood to refer to the interaction of electromagnetic radiation, electrons, or neutrons with the materials. The term "optical" typically refers to an interaction with electromagnetic radiation. For example, although electron microscopy is not always commonly considered a "spectroscopic" or "optical" method, the two terms are used inclusively herein to encompass electron microscopy and other methods of assessing interaction of a material with visible, ultraviolet, or infrared light, with neutrons, or with other radiation.

"Spectral resolution" means the ability of a radiation detection system to resolve two spectral peaks.

DETAILED DESCRIPTION

The invention relates to a method of assessing occurrence of a hazardous agent in a sample. The method comprises irradiating the sample with light and assessing Raman-shifted scattered radiation emanating from multiple points in the sample. The points having a defined geometric relationship such as a predetermined relationship or one that can be modified on demand. By way of example, points lying in a defined pattern (e.g., a circle, a line, equally spaced points, or the like) can be sampled. Alternatively, a spectroscopic property of the sample (e.g., absorbance or reflectance of light, fluorescence, dispersive Raman spectrum, or a visible optical feature, such as the size or shape of objects in the field of view of a microscope) can be examined in order to define the relationship among points to be assessed (e.g., greater point density in areas of apparent interest).

By assessing the Raman-shifted scattered radiation emitted from the points for the presence or absence of Raman shifts that are characteristic of the hazardous agent, the presence or absence of the hazardous agent in the sample can be determined. An important aspect of the invention is the discovery that the presence or absence of a hazardous agent in a sample can be accurately estimated by assessing Raman scattering from multiple points in the sample.

Samples collected from various environments (e.g.; ambient indoor and outdoor air samples, soil samples, and unknown powders) often include multiple particulate and other entities. Raman scattering analysis of such samples can be performed to identify the chemical composition of each of the entities, but such analysis can be slow, particularly where large or numerous samples are to be screened. In situations in which rapid detection of hazardous agents is desired in large or numerous samples, the capacity of traditional Raman scattering analytical methods can be overwhelmed, requiring bulky and expensive amounts of equipment to complete the analysis in a timely manner. The invention relates to the discovery that the rapidity of Raman scattering analysis can be improved by sampling multiple points in a field of view (i.e., and not sampling or scanning other areas in the field) and, if necessary, performing more detailed Raman analysis of areas and samples in which multipoint analysis indicates the presence of a hazardous agent.

Raman Spectroscopy

Raman spectroscopy provides information about the vibrational state of molecules. Many molecules have atomic bonds capable of existing in a number of vibrational states. Such molecules are able to absorb incident radiation that matches a transition between two of its allowed vibrational states and to subsequently emit the radiation. Most often, absorbed radiation is re-radiated at the same wavelength, a process designated Rayleigh or elastic scattering. In some instances, the re-radiated radiation can contain slightly more or slightly less energy than the absorbed radiation (depending on the allowable vibrational states and the initial and final vibrational states of the molecule). The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light which differs in wavelength can be more easily distinguished from the Rayleigh scattered light.

Because Raman spectroscopy is based on irradiation of a sample and detection of scattered radiation, it can be employed non-invasively and non-destructively, such that it is suitable for analysis of biological samples in situ. Thus, little or no sample preparation is required. In addition, water exhibits very little Raman scattering, and Raman spectroscopy techniques can be readily performed in aqueous environments.

The Raman spectrum of a material can reveal the molecular composition of the material, including the specific functional groups present in organic and inorganic molecules. Raman spectroscopy is useful for detection of hazardous agents because most, if not all, of these agents exhibit characteristic 'fingerprint' Raman spectra, subject to various selection rules, by which the agent can be identified. Raman peak position, peak shape, and adherence to selection rules can be used to determine molecular identity and to determine conformational information (e.g., crystalline phase, degree of order, strain, grain size) for solid materials.

In the past several years, a number of key technologies have been introduced into wide use that have enabled scientists to largely overcome the problems inherent to Raman spectroscopy. These technologies include high efficiency solid-state lasers, efficient laser rejection filters, and silicon (Si) CCD detectors. In general, the wavelength of light used to illuminate the sample is not critical, so long as the other optical elements of the system operate in the same spectral range as the light source.

In order to detect Raman scattered light and to accurately determine the Raman shift of that light, the sample should be irradiated with substantially monochromatic light, such as light having a bandwidth not greater than about 1.3 nanometers, and preferably not greater than 1.0, 0.50, or 0.25 nanometer. Suitable sources include various lasers and polychromatic light source-monochromator combinations. It is recognized that the bandwidth of the irradiating light, the resolution of the wavelength resolving element(s), and the spectral range of the detector determine how well a spectral feature can be observed, detected, or distinguished from other spectral features. The combined properties of these elements (i.e., the light source, the filter, grating, or other mechanism used to distinguish Raman scattered light by wavelength) define the spectral resolution of the Raman signal detection system. The known relationships of these elements enable the skilled artisan to select appropriate components in readily calculable ways. Limitations in spectral resolution of the system (e.g., limitations relating to the bandwidth of irradiating light) can limit the ability to resolve, detect, or distinguish spectral features. The skilled artisan understands that and how the separation and shape of Raman scattering signals can determine the acceptable limits of spectral resolution for the system for any of the Raman spectral features described herein.

To perform multipoint analysis, the sample and field to be evaluated is illuminated in whole or in part, depending on the nature of the sample and the type of multipoint sampling desired. A field of illumination can be divided into multiple adjacent, non-adjacent, or overlapping points, and Raman scattering analysis can be assessed at each of the points. By way of example, the entire sample can be illuminated and multipoint analysis performed by assessing Raman scattered radiation at selected points. Alternatively, multiple points of the sample can be illuminated, and Raman scattered radiation emanating from those points can be assessed. The points can be assessed serially (i.e., sequentially). To implement this strategy, there is an inherent trade off between acquisition time and the spatial resolution of the spectroscopic map. Each full spectrum takes a certain time to collect. The more spectra collected per unit area of a sample, the higher the apparent resolution of the spectroscopic map, but the longer the data acquisition takes. Performing single point measurements on a grid over a field of view can introduce sampling errors which makes a high definition image difficult to construct. Instead of serial analysis of sample points, Raman scattering can be assessed in parallel (i.e., simultaneously) for all selected points in an image field. This parallel processing of all points is designated Raman chemical imaging (RCI), and can require significant data acquisition time, computing time and capacity when very large numbers of spatial points and spectral channels are selected, but require less data acquisition time, computing time and capacity when relatively small number of spectral channels are assessed. Specifically, data acquisition time for RCI using tunable filter technology, a widely used configuration, requires more time as the number of spectral channels increases.

The computing and analysis resources required for multipoint analysis can be significantly less than that required for Raman chemical imaging while providing a higher number of spectral channels. An apparatus for Raman chemical imaging has been described by Treado in U.S. Pat. No. 6,002,476, and in U.S. patent application Ser. No. 09/619,371, filed 19 Jul. 2000, which are incorporated herein by reference. Other descriptions of Raman chemical imaging are U.S. patent application Ser. No. 09/800,953, filed 7 Mar. 2001; U.S. patent application Ser. No. 09/976,391, filed 21 Oct. 2001; U.S. patent application Ser. No. 10/185,090, filed 27 Jun. 2002; U.S. patent application Ser. No. 10/184,580 filed 27 Jun. 2002; U.S. provisional patent application 60/144,518, filed 19 Jul. 1999; U.S. provisional patent application 60/347, 806, filed 10 Jan. 2002; U.S. provisional patent application 60/144,518, filed 19 Jul. 1999; U.S. provisional patent application 60/187,560, filed 28 Mar. 2000; U.S. provisional patent application 60/239,969, filed 13 Nov. 2000; U.S. provisional patent application 60/301,708 filed, 28 Jun. 2001; and U.S. provisional patent application 60/422,604, filed 21 Nov. 2002. Each of the foregoing patents and applications is incorporated herein by reference.

A variety of filters and interferometers can be used to process Raman scattered light prior to analyzing it. The multiple points that are analyzed by Raman spectroscopy, as described herein, can be analyzed serially or simultaneously.

Although Raman spectroscopy can generally be applied to samples on a wide variety of surfaces, some substrate materials are preferred relative to others. Ideal substrates are optically flat, Raman inactive (i.e., exhibit little or no Raman scattering), non-fluorescent, and can sustain large laser powers without exhibiting thermal expansion. Glass-based substrates are inexpensive, commonly used, and readily available. However, some glasses exhibit significant fluorescence emission(s) that are superimposed on the Raman spectrum. Although the Raman signal can be subtracted out of the sample spectra, such subtraction contributes to noise in the resulting signal. Further, in the presence of samples with a low Raman scattering cross section (e.g., a small number of BG spores) a high background signal (e.g., that attributable to glass fluorescence) can overwhelm the Raman signal attributable to the sample. In such instances, it can be difficult to subtract out the background to reveal the sample signal. Fused silica (i.e., optical grade quartz) is an alternative often used by Raman spectroscopists, because it does not exhibit the significant fluorescence background of glass. Fused silica is also colorless and clear, allowing traditional transmittance optical viewing. Fused silica exhibits a limited Raman signal that must be subtracted from the final spectrum. Although this may present some signal-to-noise ratio problems (e.g., at very low Raman scattering cross sections), the lower background signal reduces the chance of the background signal overwhelming the sample signal, relative to glass-based substrates.

A preferred substrate is an aluminum oxide-based filter (e.g., ANODISC® brand aluminum oxide filtration membranes available from Whatman PLC, Brentford, Middlesex, UK). The ANODISC® filter exhibits a relatively weak Raman signature, is non-fluorescent, and can sustain large laser power densities without undergoing thermal expansion. Some residual spectroscopic properties of the substrate requires corrective steps to subtract its signature from the overall sample spectroscopic response, but this can be achieved using known methods. Another preferred substrate, particularly for ambient air sampling, is the micro-orifice uniform deposit impactor (MOUDI™ available from MSP Corporation, Shoreview, Minn.). This device exhibits favorable background properties. The MOUDI™ sampler collects ambient particulate material and deposits the material onto a flat, smooth aluminum foil substrate satisfactory for both Raman and scanning electron microscopic and energy dispersive spectrometric measurements. Other suitable substrates include aluminum-, silver-, or gold-coated glass slides or solid aluminum, silver, gold, or stainless steel substrates. The substrate can be structured to allow self-alignment of objects to be imaged, rendering them easier to find.

Multipoint Analysis

An important aspect of the invention is that Raman spectra are assessed at multiple points in a viewing field (e.g., the field of magnification for a microscope) that together represent only a portion of the area of the viewing field. It has been discovered that sampling the viewing field at points representing a minority of the total area of the field (e.g., at two, four, ten, fifty, one hundred, or more) points representing, in sum, 25%, 5%, 1%, or less of the field). The points can be single pixels of an image of the viewing field or areas of the field represented in an image by multiple adjacent or grouped pixels. The shape of areas or pixels assessed as individual points is not critical. For example, circular, annular, square, or rectangular areas or pixels can be assessed as individual points.

The area corresponding to each point of a multipoint analysis can be selected or generated in a variety of known ways. By way of example, a confocal mask or diffracting optical element placed in the illumination or collection optical path can limit illumination or collection to certain portions of the sample having a defined geometric relationship.

In addition to Raman spectra, other spectroscopic measurements (e.g., absorbance, fluorescence, and/or refraction) can be performed to assess one or more of the points sampled by Raman spectroscopy. This information can be used alone or as a supplement to the Raman spectral information to further characterize the portions of the sample corresponding to the individually analyzed points. This information can also be used in place of Raman spectral information. Raman spectroscopy often provides more information regarding the identity of imaged materials than many other forms of spectroscopic analysis, so inclusion of Raman spectroscopy in the methods is preferred. Additional spectroscopic information (including absorbance spectral information or image-based optical information such as the shapes of objects in the field of view) can help select a field of interest for Raman analysis, confirm the Raman spectroscopic analysis for a point, or both.

Spectroscopic analysis of multiple points in a field of view (multipoint analysis) allows high quality spectral sensing and analysis without the need to perform spectral imaging at every picture element (pixel) of an image. Optical imaging can be performed on the sample (e.g., simultaneously or separately) and the optical image can be combined with selected Raman spectrum information to define and locate regions of interest. Rapidly obtaining spectra from sufficient different locations of this region of interest at one time allows highly efficient and accurate spectral analysis and the identification of materials such as hazardous agents (e.g., BWAs and CWAs) in samples. Furthermore, identification of a region of interest in a sample or in a viewing field can be used as a signal that more detailed Raman scattering (or other) analysis of that portion of the sample or viewing field should be performed.

Multipoint analysis is diagrammed conceptually in FIG. 3. FIG. 3A shows an example of an area of the sample that can be optically viewed. FIG. 3B depicts a plurality of points superimposed on the field of view, indicating areas (i.e., points) at which Raman spectral information can be analyzed to estimate the identity of material(s) present in the field of view. Thus each point in a multipoint spectral analysis can have a unique spectrum associated with the object or material corresponding to the area.

In contrast, diagrams depicting how Raman spectral information is gathered in chemical imaging (FIG. 3C) or wide-field Raman spectroscopic (FIG. 3D) analyses are also shown. In chemical imaging, Raman spectral information is gathered for each pixel in the field, and the pixelated information is reconstructed to form an image. Although that approach is highly informative regarding the contents of the imaged field, the approach requires costly spectroscopic equipment and requires significantly more time than a multipoint approach, in which only a fraction of the information is gathered and processed. A wide-field approach requires only a single data collection (and can therefore be performed much more rapidly than chemical imaging), but averages together the spectroscopic properties of all objects in the field of view. Such averaging makes it difficult, if not impossible to identify individual components from the combined spectra, particularly when a component is present in relative small amounts. Averaged spectra can also make it difficult to determine the degree of homogeneity or heterogeneity of a sample. The multipoint spectral sensing approach described herein captures the advantages of both of these methods (i.e., full chemical imaging and wide-field Raman spectroscopy) while avoiding at least some of the drawbacks of those methods.

The multipoint method can be performed much more rapidly than chemical imaging methods, because far less raw data collection is involved. By selecting multipoint areas that are on a scale corresponding to an anticipated analyte, averaging of spectral data across the relatively limited area of each point can capture the unique spectra of the analyte. Because the multipoint area can correspond to many pixels in a full chemical image, the spectral sensing points can also improve the signal-to-noise ratio of the spectrum of each area. If the non-homogeneity of a sample can be anticipated, then the area of suitable points for Raman scattering analysis can be selected or determined based on the Raman spectra of the anticipated components and their relative amounts. Point size (i.e., the size of the area sampled in each of multiple points) can thereby be selected such that Raman characteristics of the analyte of interest (e.g., a hazardous agent) will be distinguishable from other components and anticipated background Raman scattering. The multipoint method thus can be performed with greater speed and less noise or with a greater spatial resolution and lower detection limit than the wide-field chemical imaging method.

Figure 4A:
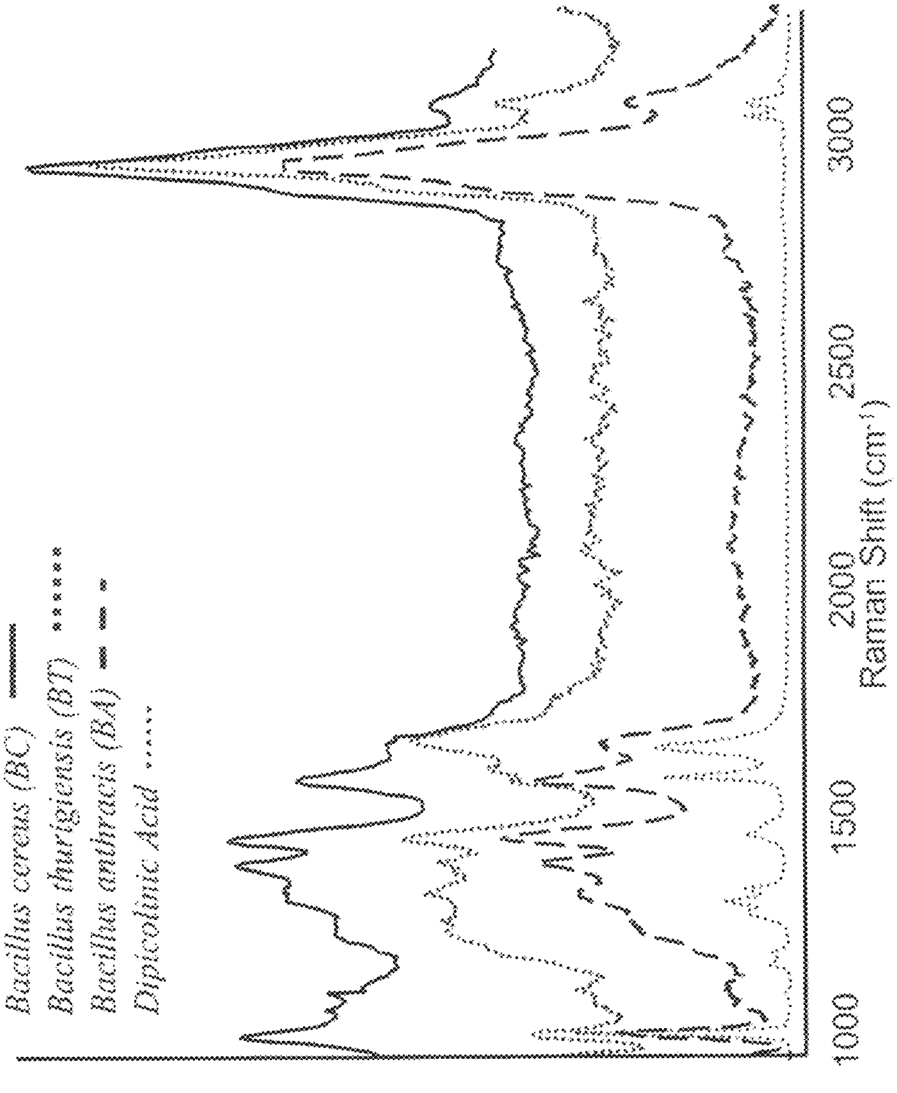
FIG. 4A is a graph of the Raman spectra of three *Bacillus* species and dipicolinic acid.
Figure 4B:
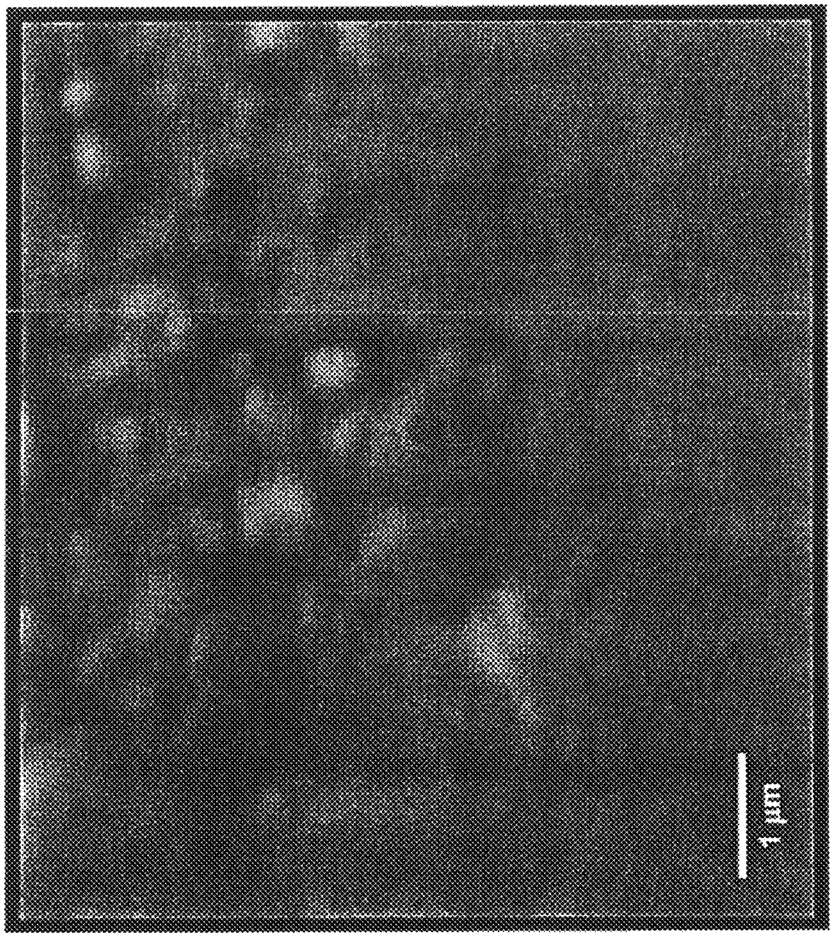
FIG. 4B is a microscopic image of *Bacillus anthracis*.
Figure 5A:
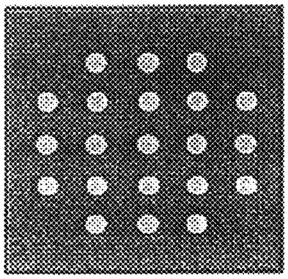
FIG. 5 shows various possible multipoint configurations for multipoint spectral sensing.
Figure 5B:
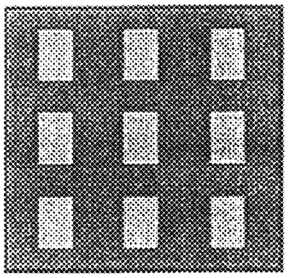
Figure 5C:
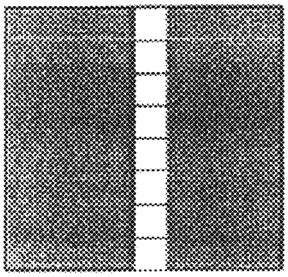
Figure 5D:
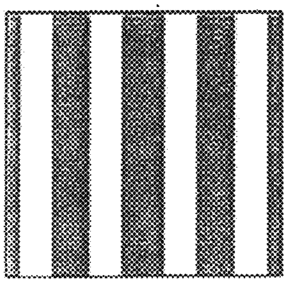
Figure 5E:
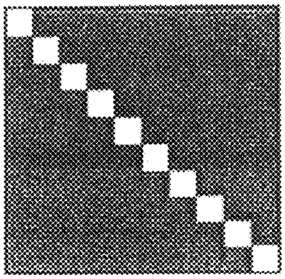
Figure 5F:
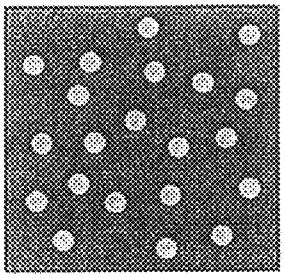
Figure 5G:
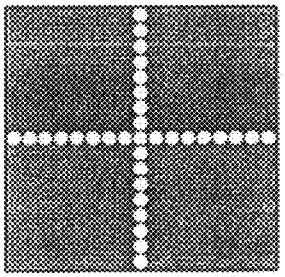
Figure 5H:
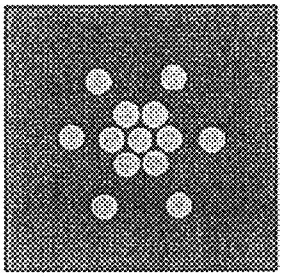

FIG. 4 shows a typical magnified view of a sample containing *Bacillus anthracis*. The spectra shown include a Raman spectrum corresponding to *B. anthracis*. The differences which are evident between the spectrum of *B. anthracis* and the spectra of the other *Bacillus* species demonstrate that *B. anthracis* can be differentiated from those species in a sample containing all three samples. This is performed by analyzing the Raman spectra of individual points in the sample and assigning an identity to the point, based on similarity to the known spectra. Any of a variety of known methods can be used to correlate the spectrum obtained at any particular point with reference spectra. By way of example, standard spectral library comparison methods can be used or the spectral unmixing methods described in U.S. patent application Ser. No. 10/812,233, filed 29 Mar. 2004 can be used. Sampling multiple points in an image allows variations in the spectra to be observed and distinctions to be made as to components present in the various portions of the sample corresponding to the points. Acquiring data at every position and analyzing the spectra at every point in an image would require significantly greater time. Multipoint spectral sensing simplifies this by focusing on specific spatial locations within the sample.

The area of points sampled can be as small as the resolution limits of the equipment used (i.e., one pixel). Preferably, multiple pixels are included in the point, so that spectral averaging methods can be used to reduce noise in the detected signal. The size of the area of each point should preferably not be greater than a small multiple of the anticipated size of the particle size of the agent to be detected. For example, in one embodiment, if the presence or absence of bacterial spores are to be analyzed, then the point size should be not greater than 2, 3, 5, 10, or 25 times the cross-sectional area of a single spore. By way of examples, bacteria and their spores have characteristic dimensions that are typically on the order of one to several micrometers, viruses have characteristic dimensions that are on the order of tens of nanometers, and eukaryotic cells have characteristic dimensions that are on the order of ten to hundreds of micrometers. The characteristic dimensions of chemical agents, including biological toxins, depend on their agglomeration, crystallization, or other associative characteristics. The characteristic size of analytes can also depend on sample components other than the analyte itself (e.g., binding or agglomerating agents).

When the area of a sample corresponding to a point at which a Raman spectrum is assessed is much larger than a characteristic dimension of an analyte or an analyte-containing particle, the methods described herein can still be employed. In that instance, the results obtained using the method will be indicative of the presence of the analyte in a region of the sample, rather than pinpointing the location of a discrete particle of the analyte. Such regions of the sample can be subjected to further analysis (e.g., finer multipoint Raman analysis or Raman chemical imaging analysis) if desired. A skilled artisan will understand how to select appropriate point sizes based on the desired analyte in view of this disclosure.

The areas corresponding to individual points in a sample need not be equal for all points in the same field of view. For example, smaller point sizes can be used in an area of the field in which finer spatial resolution is desired. Likewise, a field of view can be analyzed separately using multiple equal point sizes. By way of example, a field of view can be first analyzed at several relatively large points and, if the analyte is recognized at one of the points, a portion of the sample corresponding to that point (e.g., the quadrant of the sample that includes the point, all areas within a certain distance of the point, or the entire sample, if desired) can be re-analyzed using smaller point sizes. Multiple rounds of such analysis and point size reduction can result in images having very finely-resolved portions of interest and more crudely-resolved areas of lesser or no interest, while minimizing information processing requirements. Variable magnification or an optical zoom can be used to vary the area of the points sampled. In this way, the area corresponding to a sampled point can be matched with the size of pixels of the detector. The area of illuminated points can be controlled in the same ways (i.e., in conjunction with a grid aperture or other beam-shaping device).

Some considerations that can affect the size and shape selected for areas corresponding to individual points include the following. The size and shape can be selected to correspond to the geometry of the device used for illuminating the sample or the geometry of detector elements in the detector. The size of the hazardous agent to be detected can influence the size, shape, and spacing of the points. For instance, the area of the points can be selected so that a desired amount of hazardous agent (e.g., a single microorganism) in the point area will yield a detectable signal even if the remainder of the area is free of the hazardous agent. The minimum limit of detection desired for the hazardous agent can be determined by the proportion of the field of view that would be covered by the hazardous agent at that level, so the pattern or number of points sampled can be selected with that hazardous agent density in mind.

As illustrated in FIG. 5, a variety of configurations of the multiple points assayed as described herein can be used. In order to generate Raman-shifted scattered radiation at the multiple points, at least those points must be illuminated. The entire sample can optionally be illuminated. Raman scattering detector elements need be located only in positions corresponding to the selected points, although additional Raman detection scattering detector elements can be located in positions corresponding to portions of the sample that do not correspond to the points. Such additional detector elements can, for example, be employed for finer multipoint Raman analysis, for Raman chemical imaging, for alternative use with a different sample, or for some combination of these purposes. When Raman detector elements that do not correspond to the selected points are present, they can be (but need not be) masked, such as by manipulating the input transfer optics 200 or output transfer optics 220 of the system shown in FIG. 1. Alternatively, such unused Raman detection elements can be masked by software run by the computer 450 in the system (e.g., by simply not processing signals generated by the unused detector elements). Outputs from multiple individual Raman detection elements can be combined using known electronic and/or software methods to average the response of all detector elements corresponding to the area of a single point.

Multipoint spectral sensing can be applied separately or combined with methods of Raman, fluorescence, UV/visible absorption/reflectance, and NIR absorption/reflectance spectroscopies. Contrast can be generated in images by superimposing, adding, or otherwise combining spectral information obtained by these spectroscopic methods. Because a spectrum is generated for each point assessed in a multipoint analysis, chemometric analysis tools such as correlation analysis, principal component analysis (PCA), and factor rotation, including multivariate curve resolution (MCR), can be applied to the image data to extract pertinent information that might be less obvious by analyzing only ordinary univariate measures.

Furthermore, regions of a sample suitable for multipoint Raman scattering analysis can be identified by first using other optical or spectroscopic methods. By way of example, in a method for assessing the presence of a pathogenic bacterium, optical microscopy can be used to identify regions of a sample that contain entities having the size and/or shape of bacteria. Fluorescence analysis can be used to assess whether the entities identified by optical microscopy appear to be of biological origin (i.e., by exhibiting fluorescence characteristic of bacteria). For portions of the sample containing entities which appear to have the size and/or shape of bacteria and exhibit apparently biotic fluorescence, Raman scattering analysis can be performed at multiple points within that portion, as described herein. Further by way of example, near infrared (NIR) imaging can be used to identify suspicious portions of a parcel that is not transparent to visible light, and to perform multipoint Raman scattering analysis on those suspicious portions, as illustrated in FIG. 10.

By way of example, the intensity of radiation assessed at one Raman shift value can be superimposed on a black-and-white optical image of the sample using intensity of red color corresponding to intensity of the Raman-shifted radiation at a particular Raman shift value, the intensity of radiation assessed at a second Raman shift value can be superimposed on the image using intensity of blue color corresponding to intensity of the second Raman-shifted radiation, and the intensity of fluorescent radiation assessed at one fluorescent wavelength can be superimposed on the image using intensity of green color corresponding to intensity of the fluorescent radiation. Further by way of example, if the characteristics of a portion of the image are within the limits of predetermined criteria for detecting the presence of a hazardous agent, the portion of the image for which the characteristics meet those criteria can be made to switch on-and-off or to otherwise indicate the presence of the detected agent.

Depending on the materials and the spectroscopic method(s) used, depth-related information can also be obtained by using different excitation wavelengths or by capturing spectroscopic images at incremental planes of focus. Thus, depending on the penetrating ability of illumination and detected wavelengths, the contents of objects (e.g., vials, envelopes, or suitcases) can be assessed using these methods.

A spatial resolving power of approximately 250 nanometers has been demonstrated for Raman spectroscopic imaging using visible laser wavelengths and commercially available devices. This is almost two orders of magnitude better than infrared imaging, which is typically limited to a resolution not better than 20 micrometers, owing to diffraction for example. Thus, multipoint size definition performed using Raman spectroscopy can be higher than other spectroscopic methods and Raman methods can be used to differentiate spectral features of small objects. Simplified designs of detectors (i.e., relative to chemical imaging devices) are possible since spectroscopic imaging and the assembly of a spectral image is not necessary in this approach.

An advantage of using NIR radiation in multipoint spectral sensing is that it penetrates more deeply than visible light so as to enable one to probe inside of paper or plastic envelopes or plastic or glass containers, for example to detect a hazardous agent in such a container. Any container that does not totally absorb the incident radiation can be examined using the NIR multipoint spectral sensing approach.

Examples

The invention is now described with reference to the following Examples. These Examples are provided for the purpose of illustration only, and the invention is not limited to these Examples, but rather encompasses all variations which are evident as a result of the teaching provided herein.

Rapid Hazardous Agent Detection System

The overall schematic of a hazardous agent detection system that uses multipoint detection is shown in FIG. 1. Such systems can be used or modified as described herein to meet the instrument requirements of the methods described herein for multipoint hazardous agent detection systems. These configurations include platforms based on a telescope, a microscope, a macroscope, an endoscope, a fiber array spectral translator (FAST), or an air- or water-sampler design. Each of these is outlined in the following sections.

In FIG. 1, excitation sources 110, 120, 130, and 140 (corresponding to near infrared, infrared, visible, and ultraviolet sources, any combination of which can be present) provide incident radiation that is directed by input transfer optics 200 onto a sample that is situated in a sample cell 210. The excitation sources can be substantially any known radiation source, including polychromatic sources such as tungsten or mercury arc lamps and substantially monochromatic sources such as lasers and light-emitting diodes. If a polychromatic source is used for Raman scattering analysis, a filter, grating, or other device(s) should be used to isolate substantially monochromatic light from the source, for example as a part of the input transfer optics 200.

Radiation transmitted through, or reflected, refracted, emitted, or scattered by the sample is collected using output transfer optics 220 selected and situated to be appropriate for the radiation to be collected. The collected radiation is directed to appropriate detectors, and the output of the detectors (informative of the collected radiation) is captured by a data recordation circuit or device, which can be physically and/or electronically integrated with the detectors (as in the integrated optical detectors and data capture subsystem 300 depicted in FIG. 1).

Figure 2:
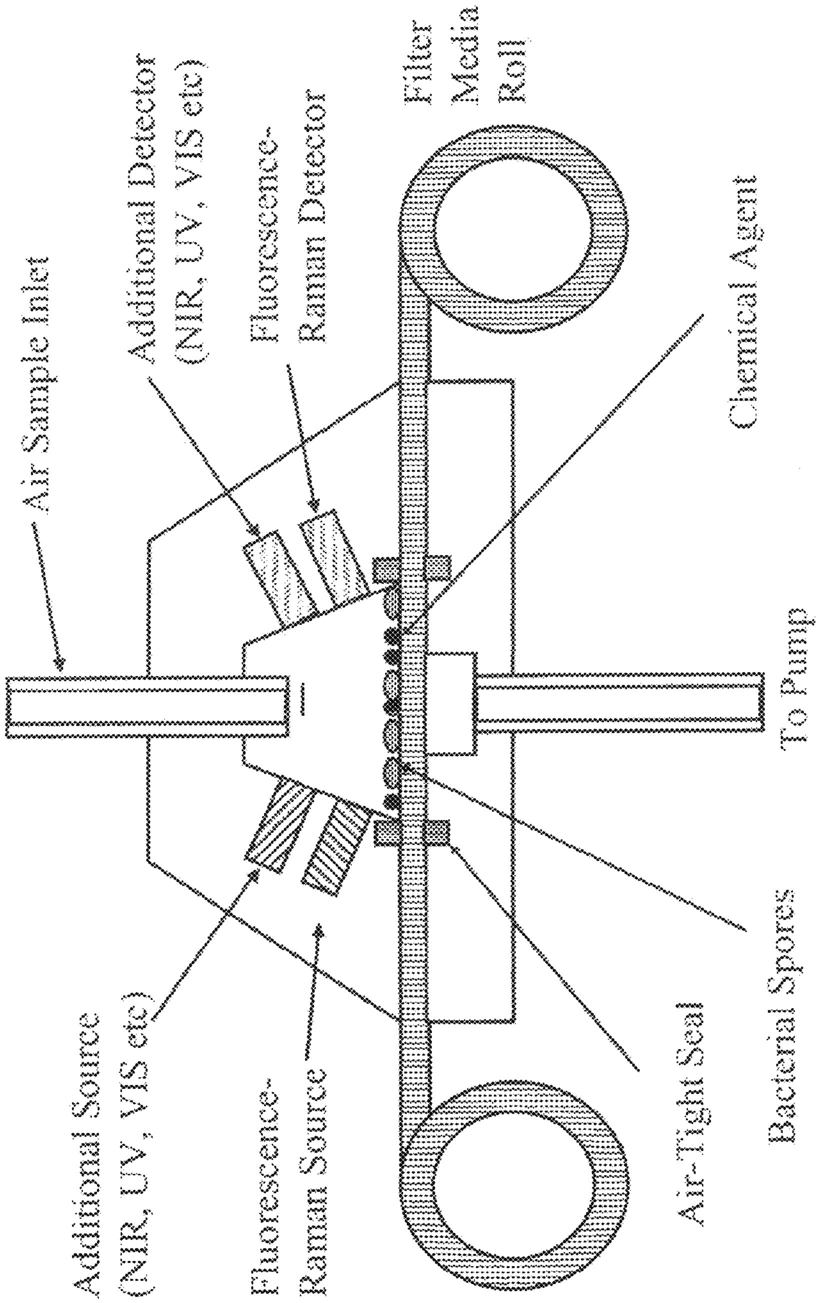
FIG. 2 is a schematic diagram of an ambient air sensor suitable for use in multipoint sensing and detection of BWA and CWA in systems described herein.
Figure 3A:
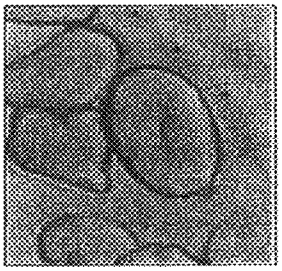
FIG. 3 compares an optical image (FIG. 3A) of a field of view for a sample with an image showing suitable sampling points areas for multipoint Raman spectral analysis (FIG. 3B), an image representing every pixel of the viewing field, such as can be used for Raman chemical imaging (FIG. 3C), and an image showing an integrated area useful for a wide-field Raman spectral analysis (FIG. 3D).
Figure 3B:
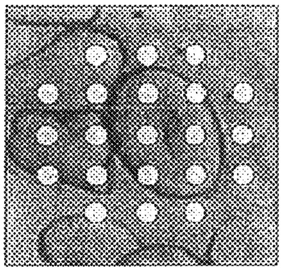
Figure 3C:
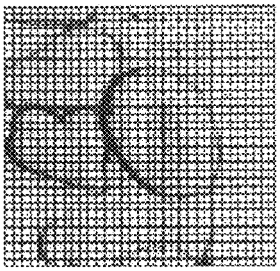
Figure 3D:
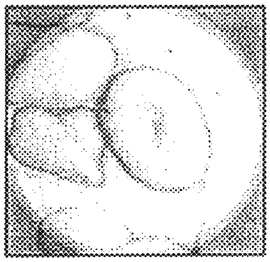

Data collected from the detectors is preferably fed into a data analysis subsystem 400 within or linked to a computer 450. The computer can be operated with software for controlling illumination, data collection, sample positioning, and the like, and such software is within the ordinary level of skill in this field and commercially available. The computer preferably links input 410, display 420 (e.g., a visual display such as a video display terminal or printable image), and data storage 430 functions with the optical device(s), and also preferably is able to format output/results 500 in a way convenient for the user. By way of example, the sample cell can be configured to optimize hazardous agent detection for different environments. FIG. 2 shows a cell for air sampling where a sample collection substrate is fed continuously into the sample cell 210, the computer 450 may conveniently provide output 500 that indicates the number of entities that are detected on the substrate as having Raman spectral characteristics of the hazardous agent of interest during a given period of time. Further, the output 500 may trigger an alarm circuit if the number of hazardous agent entities detected during a period of time (or during multiple consecutive periods of time) exceeds a preselected value. Alternatively, data collected from the detectors can be displayed for analysis by a user, and portions of the sample can be selected by the user for finer multipoint Raman scattering analysis or for Raman chemical imaging.

An example of a commercially available device which is suitable for use in one or more of the platforms is a laboratory or transportable field Raman microscope such as the FALCON or EAGLE™ Raman microscopes (ChemImage Corporation, Pittsburgh, Pa.) outfitted with the simultaneous imaging and spectroscopy apparatus and software offered by that supplier for use with the instrument. Another example of a suitable instrument upon which such systems can be based is an ultraviolet (UV)/visible (vis)/near infrared (NIR) fluorescence or Raman macroscope, or a UV/Vis/NIR/Mid-IR (mid-infrared) absorption/reflectance macroscope system such as the CONDOR™ Macroscope (ChemImage Corporation, Pittsburgh, Pa.). Another suitable device is a laboratory or field fiberscope such as the RAVEN™ endoscope (ChemImage Corporation, Pittsburgh, Pa.). Other suitable devices are described in U.S. Pat. No. 6,002,476. Any of these instruments can be used alone or with additional optics, such as a laboratory or field Fiber-Array Spectral Translator (FAST) probe. Each of the modes of application can be used separately or in combination with one another to achieve the desired speed and results.

These systems can be automated through the use of robotics or combined macro/micro instrumentation in order to target analytes of interest. Using laser ablation and/or chemical ablation, the system can be automated to eradicate hazardous agents post-targeting, for example. Such a system should provide fast acquisition times (on the order of seconds), high spatial resolution (sub-micron), and good spectral resolution (<200 nanometers).

Microscope-Based System

A multipoint Raman spectroscopic imaging microscope combines in a single platform a solid state laser for sample excitation (e.g., for Raman analysis, laser-induced fluorescence, or both), a refractive optical microscope base, which is equipped with infinity-corrected microscope objectives, an automated XYZ translational microscope stage, and a quartz tungsten halogen (QTH) lamp and/or a mercury (Hg) lamp. Also a part of the microscope system is an analog color charge-coupled device (CCD) detector for ordinary optical image collection and digital image collection, a liquid crystal spectrometer or other multipoint spectrometer technology including AOTF, scanned linearly variable or rotated circularly variable dielectric filters, angle-rotated Fabry Perot dielectric or other bandpass filter, interferometers including Michelson and Zagnac types, or dispersive spectrometers. Also included is either a room temperature or optionally cooled photomultiplier, IR FPA for IR image capture or a liquid nitrogen- or thermoelectrically-cooled (TE) Si CCD or complementary metal oxide semiconductor (CMOS) detector for UV/visible, Raman and fluorescence data capture, and a remote, dispersive monochromator equipped with a CCD or CMOS detector for single point or multipoint dispersive spectral collection. Other known detectors can be used, including avalanche photodiode detectors, charge injector device detectors, electron multiplying CCDs, intensified CCDs, linear array detectors, and others.

UV, visible, or NIR illumination is directed to the sample in a reflected light configuration using a QTH source or other broadband white light source, including metal halide, Hg arc lamps, or Xe arc lamps or a transmitted light configuration using QTH or other suitable source of a refractive optical microscope platform. In a Raman or laser-induced fluorescence experiment, laser radiation is introduced to the sample through use of a Raman illuminator. Light scattered, emitted, reflected, or transmitted is collected from the sample positioned on the automated XYZ translational microscope stage through light gathering optic, such as an infinity-corrected microscope objective.

Ordinary optical imagery of the sample can be obtained using a mirror or beamsplitter or prism arrangement inserted into a turret wheel of the microscope by collecting an image with an analog or digital color or monochrome (e.g., CCD or CMOS) detector. In spectroscopic imaging mode, the magnified spectroscopic image is coupled through an imaging spectrometer and collected on a NIR or mid-IR focal plane array (FPA) detector (for IR spectroscopic imaging) or a Si CCD detector (for UV/visible absorption/reflectance, fluorescence, or Raman spectroscopic imaging). A suitable IR FPA can be comprised of indium gallium arsenide (InGaAs), but may be comprised of other IR sensitive materials, including platinum silicide (PtSi), indium antimonide (InSb), or mercury cadmium telluride (HgCdTe).

A central processing unit, such as a PENTIUM® processor-based computer, can be used for spectroscopic image collection and processing, including definition and data collection at the individual points of a multipoint Raman analysis. The analog color CCD, IR FPA, Si CCD, automated XYZ translational microscope stage, liquid crystal tunable filter, an imaging spectrometer, other components of the instruments, or some combination of these can be controlled by the computer. Commercial software packages, such as CHEMACQUIRE™ (ChemImage Corporation, Pittsburgh, Pa.), CHEMANALYZE™ (ChemImage Corporation, Pittsburgh, Pa.), and CHEMIMAGE XPERT™ (ChemImage Corporation, Pittsburgh, Pa.) are available for such control, and it is within the ordinary level of skill in this field to modify existing software or generate new software for control of the instruments described herein.

By including a polarization sensitive beam splitting element in the optical path prior to the liquid crystal imaging spectrometer, a portion of the signal from the sample can be coupled to a remote dispersive spectrometer. This allows conventional spectroscopic tools to be used to gather spectra for traditional, high-speed spectral analysis prior to or in conjunction with multipoint Raman analysis. The spectrometers can include one or more of the following types: fixed filter spectrometers, dispersive spectrometers, Fourier transform spectrometers, and acousto-optic spectrometers. A polarization independent interferometer such as a Michelson interferometer, a Sagnac interferometer, a Twynam-Green Interferometer, or a Mach-Zehnder Interferometer can be used as a filter.

Liquid crystal (LC) sensing spectrometer technology is used for wavelength selection. The LC sensing spectrometer may be of the following types: Lyot liquid crystal tunable filter (LCTF); Evans Split-Element LCTF; Solc LCTF; Ferroelectric LCTF; Liquid crystal Fabry Perot (LCFP); or a hybrid filter technology comprised of a combination of the above-mentioned LC filter types. Additionally, fixed bandpass and band rejection filters comprised of dielectric, rugate, holographic, color absorption, acousto-optic, or polarization types may also be used, either alone or in combination with one of the above LC spectrometers. Novel tunable filter designs identified as bi-refringent interference spectrally agile filter element (BISAFE) as well as micro-opto-electromechanical (MOEM) based spectrometers have characteristics that enable multipoint imaging with a smaller form factor than conventional filter designs and are suitable for use in handheld and portable devices.

New solid state multipoint detector designs can also reduce the cost of the detector without compromising the ability to perform multipoint spectral sensing The BISAFE filter, which is described in co-pending U.S. patent application Ser. No. 10/893,331, filed on 19 Jul. 2004 and in U.S. provisional patent application No. 60/488,246, filed on 18 Jul. 2003, is a linearly tunable filter that allows line imaging. Spectral data is obtained in different spectral ranges and at different locations (i.e., lines) of the sample simultaneously. Similarly, the MOEMS filter, which is described in co-pending U.S. patent application Ser. No. 10/893,332, filed on 19 Jul. 2004 and in U.S. provisional patent application No. 60/488,246, filed on 18 Jul. 2003, senses different spectral regions along strips of the silicon plates forming this MOEMS device. These strips define the regions selected on the sample by positioning plates using MEMS microactuators. Images can be reconstructed if desired by stepping the sample position. This device can operate either in a transmission mode in which the light travels parallel to the substrate and normal to the Si plates, or in a transmission-reflection mode in which light travels normal to the substrate and normal to the silicon plates. Such devices allow a trade-off between selection of spatial position or spectral resolution in a simple design.

Dispersive spectrometers can be used with FAST technology for wavelength and multipoint spectra collection. Such spectrometers can allow a line of points along the sample to be sampled at each wavelength setting of the spectrometer during each measurement. This allows efficient data collection of many points at the same time thereby providing many spatially distinct spectra to be obtained at once during one scan over the spectral regions of interest.

The multipoint spectral sensing microscope can also be used as a volumetric imaging instrument by moving the sample through the focus plane in the Z-axial dimension (i.e., in a direction normal to the two-dimensional X/Y plane of image analysis), collecting images in and out of focus and reconstructing a volumetric data of the sample using appropriate software, which is commercially available and/or within the ordinary level of skill in this field. For samples having significant volume (e.g., bulk materials, surfaces, interfaces, and phase contact regions), volumetric spectroscopic reconstruction is useful for failure analysis, product development, and routine quality monitoring. Quantitative analysis can be performed simultaneously with volumetric analysis. Volumetric analysis can be performed in a non-contact mode without modifying the sample by using numerical confocal techniques, which require that the sample be sensed at discrete focal planes. Computational optical sectioning reconstruction techniques based on a variety of strategies have been demonstrated, including nearest neighbors and iterative deconvolution, and such computational methods are suitable for use with the devices and methods described herein.

Microscope-based spectroscopic sensing systems have the advantage of being able to detect, classify, identify, and visualize entities such as BWAs at the level of a single bacterium, for instance. These systems exhibit a spectral resolution on the order of 8 $cm^{-1}$ and a spatial resolution of approximately 200 nanometers using numerical deconvolution methods.

Macroscope-Based System

The spectroscopic multipoint sensing macroscope combines in a single platform an illumination subassembly consisting of an illumination source (e.g., a QTH, Xe, Hg, or metal halide lamp), a barrier optical filter(s), and a light-directing module (i.e., direct beam, fiber optic, or liquid light guide illumination). A radiation detector such as an analog color CCD detector is used for ordinary optical and digital image collection. Wavelength selection for Raman scattering illumination is performed using a LCTF, filter/grating, and aperture combination, or other suitable monochromator, or simply by illuminating the sample with a substantially monochromatic source such as a laser. The imaging detector can be either a room temperature or optionally cooled NIR FPA (for NIR image capture) or a TE Si CCD detector (for UV/visible and fluorescence image capture), for example. Suitable Raman scattered light detectors are described elsewhere herein.

UV, visible or NIR illumination is directed to the sample in a reflected light configuration using a QTH source or other broadband white light source, including metal halide, Hg arc lamps, or Xe arc lamps or a transmitted light configuration using QTH or other suitable source through direct illumination, fiber optics or liquid light guides. Light emitted, reflected or transmitted is collected from the sample positioned on the macroscopic sample base through a macro lens.

Ordinary optical imagery of the sample may be obtained using a mirror or beamsplitter or prism arrangement inserted into the collection stack of the macroscope and collecting an image with an analog or digital color or monochrome CCD or CMOS detector. In spectroscopic mode, the spectroscopic points sampled are coupled through a liquid crystal spectrometer and collected on a NIR FPA detector (for NIR spectroscopic imaging) or a Si CCD detector (for UV/visible absorption/reflectance, fluorescence and Raman spectroscopic imaging). A computer, such as a PENTIUM® processor-based computer, can be used for multipoint spectroscopic data collection and processing as described herein.

Liquid crystal (LC) spectrometer technology can be used for Raman scattered light wavelength selection. The LC spectrometer can be of any of the types described herein. Additionally, fixed bandpass and bandreject filters of the types described herein can be used, either alone or in combination with an LC spectrometer. These filters can select an arbitrary or random set of points for sampling or a well defined set of points determined by the sampling approach and/or the requirements for high performance of the spectrometer. For example, a resistive anode array used as a photon detector favors selection of linear points along the sample. Similarly a FAST array can be arranged in linear fashion or other collection geometry to facilitate data acquisition.

Grating spectrometers can be used in the FAST configuration for wavelength and multipoint spectra collection. Such spectrometers used with FAST technology allow an arbitrary arrangement of points on the sample to be sampled at each wavelength setting of the spectrometer. This allows efficient data collection of many points at the same time and collection of spatially distinct spectra during a single scan over the spectral regions of interest.

A macroscopic-based system enables rapid detection of potential BWAs and CWAs over a large area, such as the surfaces and contents of envelopes and packages received by mail and analysis of surfaces in remote locations. In multipoint detection, rapid sampling strategies (e.g., sampling of few, relatively distantly-spaced points) enables finer (sampling of more, relatively more closely-spaced points) analysis of sample regions of interest.

Endoscope-Based System

Spectroscopic sensing has traditionally been performed in laboratory settings using research-grade light microscope technology as an image-gathering platform for selection of specific points. However, multipoint spectroscopic sensing is also applicable to in situ industrial process monitoring and in vivo clinical analysis. The application of multipoint spectroscopic sensing outside the research laboratory has been limited by the lack of availability of stable multipoint selection/detection platforms that are compatible with the physical demands of industrial process monitoring and clinical environments. Both industrial and clinical settings often require compact, lightweight instrumentation suitable for the examination of remote areas that are inaccessible to conventional spectroscopic instrumentation.

A robust spectroscopic multipoint design employing liquid crystal technology is described herein, and the equipment, systems, and methods described herein can be employed using fiber optic technology suitable for fashioning into a flexible probe such as an endoscope. The liquid crystal endoscope is the first flexible multipoint endoscopic technology that provides real-time video inspection capability with multipoint Raman spectral analysis. The endoscope, comprising from two to thousands of independent fibers arranged in a fiber bundle, couples to a video CCD for real-time video imaging of the analysis area. This allows for quick visual screening of the sample. The endoscope tip is engineered to filter laser illumination and collect Raman scattered radiation and fluorescent emissions (for Raman and fluorescence applications, respectively). The light from the laser delivery fiber is filtered so that substantially only the laser wavelength is presented to the sample. The laser light is removed from the collected light so that Raman information is detectable to within 200 $cm^{-1}$ of the laser line. The distal end of the liquid crystal Raman endoscope is environmentally resistant and can withstand continuous operation at high temperatures and has been demonstrated to operate from 0 to 315 degrees Celsius while maintaining high signal to background performance. The distal end can be coupled to a microscope-based system enabling dispersive spectroscopy and multipoint spectroscopic sensing to be performed remotely.

An endoscope-based spectroscopic sensing system is useful for detecting the presence of a hazardous agent in a remote location, such as the interior of a box or envelope, for example.

FAST-Based System

An emerging technology in the field of spectroscopic imaging is the use of fiber optic arrays. We have termed this technology Fiber Array Spectral Translators (FAST) but it is also accurately described as dimension reduction arrays. FAST technology can acquire a few to thousands of full spectral range, spatially resolved spectra simultaneously. For imaging this is done by focusing a spectroscopic image onto a two dimensional array of optical fibers that are drawn into a one-dimensional distal array with serpentine ordering. The one dimensional fiber stack is coupled to an imaging spectrograph. Software then extracts the spectral/spatial information that is embedded in a single CCD image frame. Fiber array spectroscopic imaging has been demonstrated in several applications including Raman chemical imaging analysis of micro-composites and biomaterials and time-resolved atomic emission chemical imaging of laser-induced plumes.

The high numbers of optical fibers required for FAST imaging applications place extraordinary demands on the imaging spectrograph which the multipoint method addresses. Instead of having millions of pixels, multipoint analysis can utilize larger diameter fibers in bundles containing tens to hundreds of fibers. In the multipoint method of spectral sensing and analysis, complete spectral imaging (which would requires at least thousands of adjacent pixels to create a physical image) is not required. Instead, spectral sensing performed at tens to hundreds of points simultaneously can rapidly (on the order of seconds) provide high quality spatially resolved spectra from a wide variety of points on the sample needed for analysis and identification. Thus, even if the precise geometric arrangement of the points analyzed in the field of view is not known; the points nonetheless have a defined geometrical arrangement which can span a sample or a field of view. The analyzed points are informative regarding the presence and, if present, the amount of a hazardous agent of interest in a sample.

An advantage of this method over other current point spectroscopic detection methods is speed of analysis. A complete spectroscopic multipoint data set can be acquired in the amount of time it takes to generate a single spectrum from a given material. Even with limited pixel definition, superimposing color-coded multipoint spectral data obtained from known areas of a field of view on high-spatial resolution gray-scale images can provide significant insight into the morphology and chemistry of materials.

Ambient Air Sensor System

The invention includes an ambient air sensor system comprising two parts, a sampling system and a spectroscopic imaging system. The optics block of such a system is shown diagrammatically in FIG. 2. This block supports a section of a sample collection substrate such as a filter medium (e.g., a microporous filter medium having pores sufficiently small to substantially prevent passage of the hazardous agent of interest or a coated filter medium having pores large enough to permit passage of the hazardous agent of interest, but coated with an oil or other substance to which passing hazardous agent particles can adhere or into which passing molecules can be absorbed or dissolved) and provides an airtight seal around the periphery of the sampling area. This block should be easily opened so that either a new filter (when the system uses discrete filters as the substrate) or a new section of filter (when the system uses a continuous filter substrate) can be placed in the sampling/optics path. When a continuous substrate is used, a drive (e.g., a manual crank or a motor) can be included to advance the substrate between measurements, so that a fresh piece of the substrate is used for each measurement. The drive can be controlled by the same controller (or computer, if separate) used to control the optics.

The sampling system has an inlet, which is open to the atmosphere being tested. Its dimensions are optimized for the sampling flow rate and the anticipated range of particle sizes. For particulate or aerosol sampling, it is important that the inlet have no sharp bends or areas of low linear velocity, which can cause deposition of particulate prior to the collection filter. The sampling system includes or is connected to a sampling pump, which provides negative pressure to pull ambient air through the filter. Operation using positive pressure to force ambient air against the substrate is also possible. Air flow rates are in the range from 0.5 to 2.0 liters per minute are considered suitable for sampling, and a vacuum of about 100 inches of water (180 millimeters of mercury) should suffice to collect particulates in such a volume in a reasonable sample substrate area.

The sampling system can be operated continuously or, preferably, during a series of discrete sampling periods. At the end of each period, the sample collection substrate can be replaced (or advanced if a continuous medium is used). This can be done either by the operator or automatically. For continuous or interrupted sampling, the substrate can be in a tape-like filter configuration and new samples of filter can be positioned in the optics block by a tape-drive mechanism, similar to that of an audiocassette. A wide variety of appropriate sample collection medium are known, including filter media such as porous polypropylene media and aluminum media, in disk, sheet, and roll forms. Selection of an appropriate sample collection substrate is within the ken of a skilled artisan. Other examples of substrates for collection of samples include glass slides, fused silica slides, ceramic materials, semiconductor materials (e.g., silicon), polymers (e.g., polycarbonates or TEFLON™), metal substrates (e.g., aluminum, silver, gold, or stainless steel), metal-coated slides or polymer strips (e.g., aluminum-coated glass slides or MYLAR™ films). If desired, the surface of the substrate can be coated with known agents such as silanes and charge- and pH-modifying agents.

Once the particulates have been trapped on the sample collection substrate, multipoint spectroscopy is used to detect and classify any hazardous agent that is present. If the excitation source is a laser, coupled to the optics block using conventional or fiber optics, whose light is distributed over the multipoint sampling area, Raman imaging can be used. Alternately, the laser light can be shaped in this projection process to match the distribution of points being selected (e.g., based on the predetermined points to be analyzed) or sampled. In another configuration, a light source comprised of a broadband UV/Visible (UV/Vis), filtered UV/Vis, or a UV/V is laser can be used to excite autofluorescence. The multipoint detector can be of the liquid crystal tunable type or another multipoint spectrometer type as described herein, and a CCD or other array camera can be used to define the sampling area at multiple wavelengths. Coupling of the detector to the optics block can be through fiber-based or conventional optics. The detector data is processed using chemometric and data analysis tools such as those found in the CHEMANALYZE™ and CHEMIMAGE XPERT™ software packages (ChemImage Corporation, Pittsburgh, Pa.).

The ambient air monitor can be operated intermittently, for example as a series of sampling periods during which periodic spectroscopic measurements are taken. The sampling periods can follow one another immediately (i.e., a subsequent sampling period begins immediately following the preceding sampling period) or be interrupted by a period of time (e.g., sampling periods interrupted by a 20 minute delay). The results from the previous and current sampling periods can interpreted by a system computer which can display results and activate warning and danger alarms, or initiate some action such as turning off a building outside air intake. Air monitoring can also be performed remotely using a telescopic adaptation of this approach.

Experimental Results

Figure 6A:
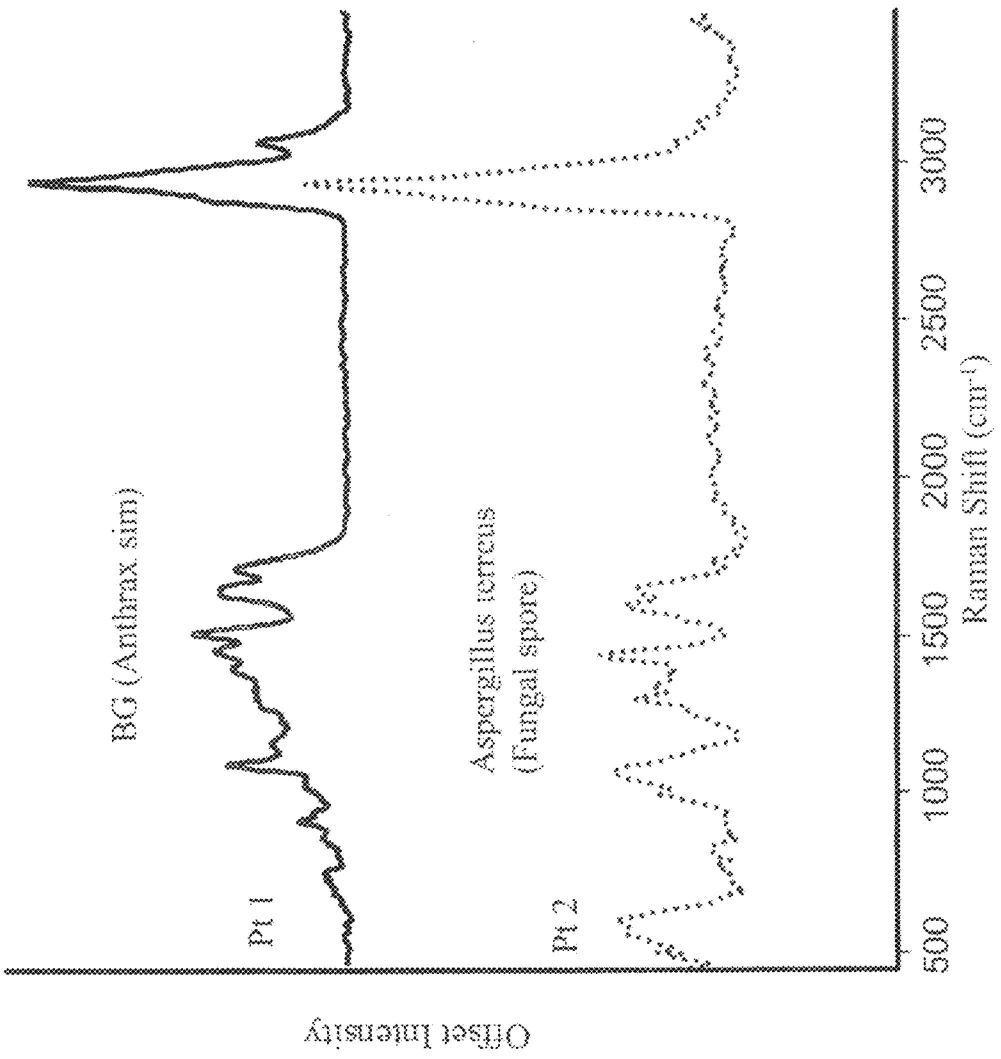
FIG. 6A depicts Raman spectra of *Bacillus globigii* (BG, an anthrax simulant; points 1 in color FIG. 6B) and *Aspergillis terreus* (Fungal spores; point 2 in color FIG. 6B).
Figure 6B:
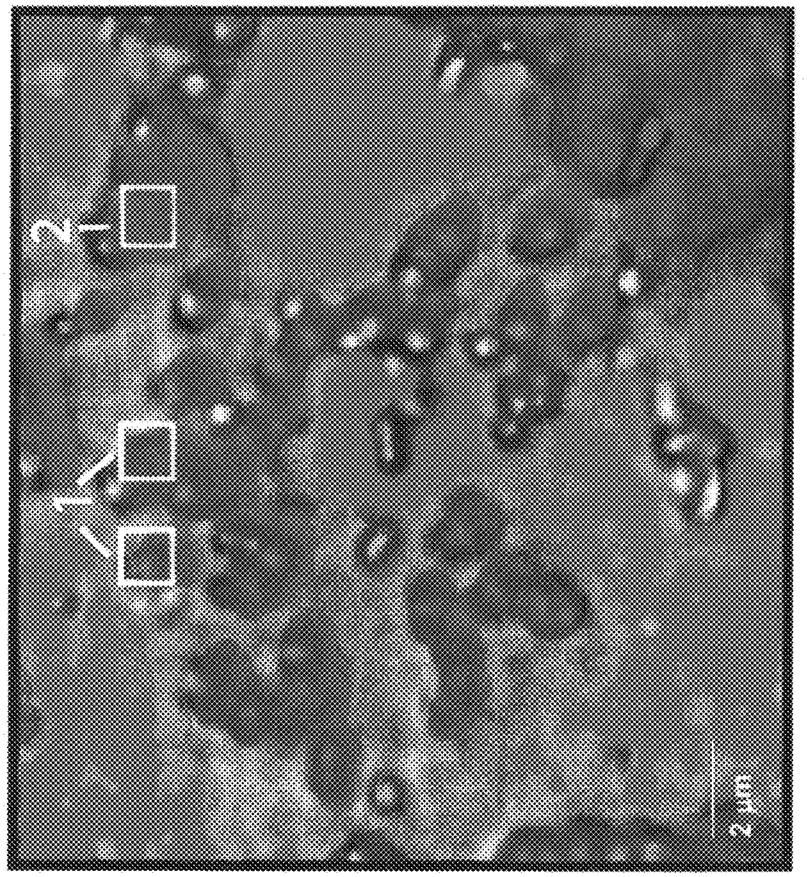
FIG. 6 consists of FIGS. 6A and 6B.

Spectra generated using Raman spectroscopic methods can potentially reveal a wealth of information about molecular properties of hazardous agents. Raman scattering analysis allows variations in the composition of the materials at analyzed points to be probed downed to arbitrarily small levels (e.g., a single bacterium) if desired. FIG. 6A, for example, shows Raman spectroscopic multipoint spectra from a mixture of *Bacillus globigii* (BG, an anthrax simulant) and *Aspergillis terreus* (a fungus) spores. The optical image and multipoint regions sampled are also indicated. The Raman spectra in FIG. 6A show the spectral "fingerprints" obtained for the multipoint spectral sensing at the indicated regions of FIG. 6B. These spectral differences clearly distinguish BG from the fungal spores. Despite the morphological similarities between the mixture components seen in FIG. 6B, the Raman spectra distinguish the two distinct species. This ability to characterize bacteria spores in the presence of non-threatening 'masking' agents is a critical issue in the detection and identification of hazardous agents, and these results demonstrate that the methods described herein are able to discriminate hazardous and masking agents. Such agents can also be detected in water or in water-containing environments.

Traditional methods can differentiate spores from different bacterial species only with difficulty. FIG. 4 depicts dispersive Raman spectra take from three different samples, each comprising one bacterial spore type. The Raman spectrum of dipicolinic acid (a major component of spores of the genus *Bacillus*) is also shown. These spectra demonstrate that despite the genetic and morphological similarities among the spores, Raman spectroscopy can discriminate among the different bacteria spores. The ability to distinguish the different spectra of small objects during a single Raman spectral scan is important for picking out and discriminating entities such as BWAs or CWAs in a mixture.

Raman spectra of *Bacillus anthracis* (anthrax) spores have been determined in a secure biohazard laboratory, and those spectra are available to the public (e.g. presented at the 2004 annual meeting of the Federation for Analytical Chemist and Spectroscopy Societies in Portland, Oreg. on 4 Oct. 2004).

Different strains of anthrax spores can differentiated by Raman spectroscopy and Raman Imaging. Additionally, multipoint Raman spectral analysis has been used to differentiate same species and strain grown under different environmental conditions and/or growth medium.

The ability to differentiate the strain and growth conditions of an anthrax spore sample can be useful for investigating the source, age, storage conditions, method of production, and other relevant characteristics of the sample. Similarly, Raman multipoint spectral analysis has been used to differentiate viable from non-viable endospores. Viability of suspect spores is a critical variable in determining the real threat posed.

Figure 7A:
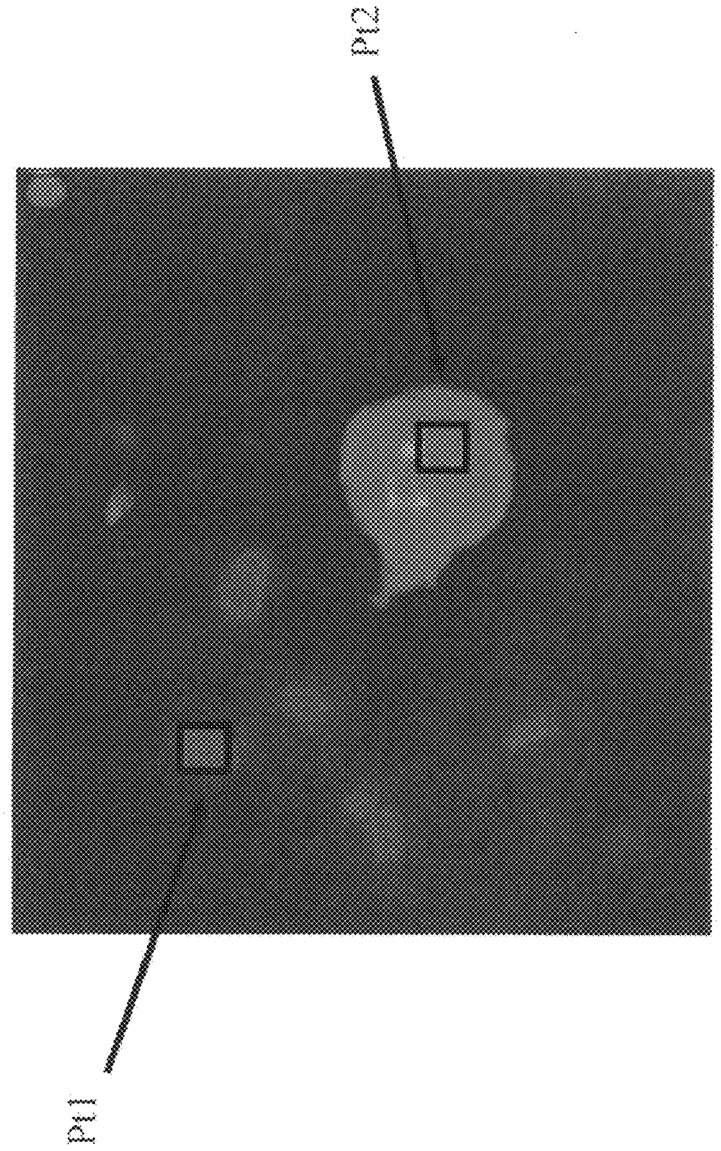
FIG. 7A is a color fluorescent image of the mixture.
Figure 7B:
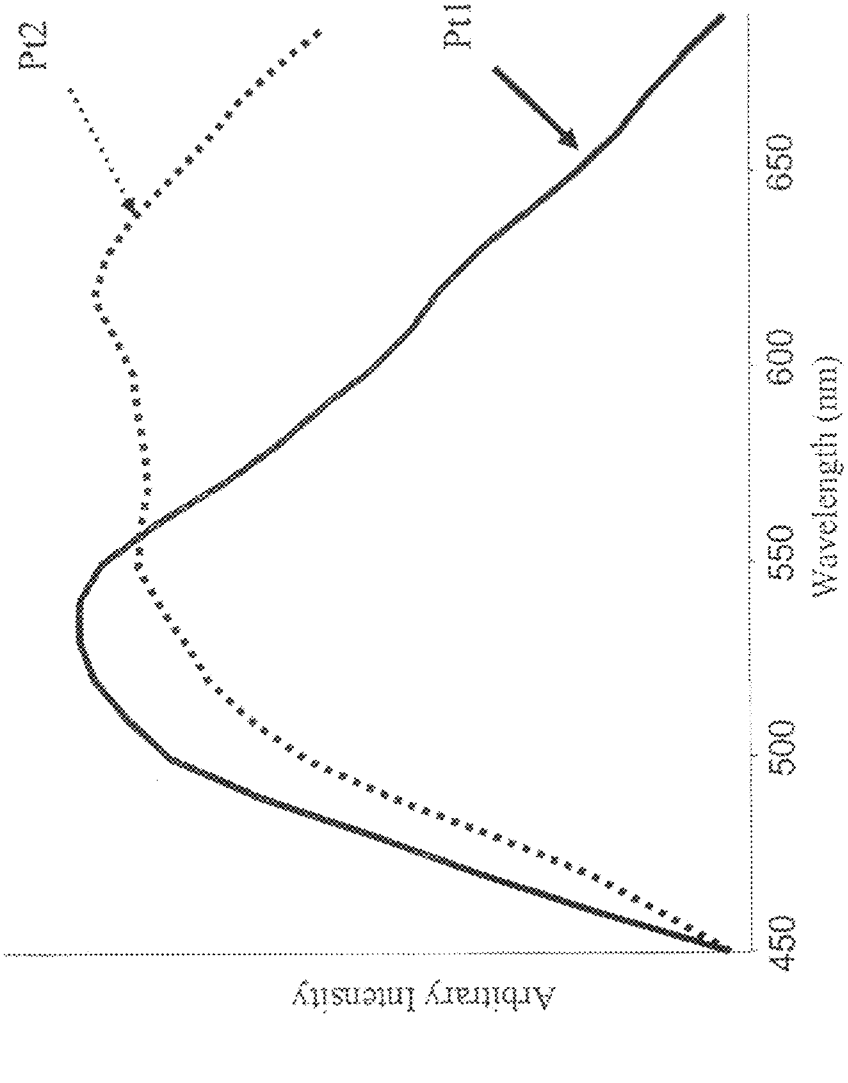
FIG. 7B depicts fluorescence spectra characteristic of *B. pumilus* (Pt1 in FIG. 7A) and *B. subtilis* (Pt2 in FIG. 7A).
Figure 8A:
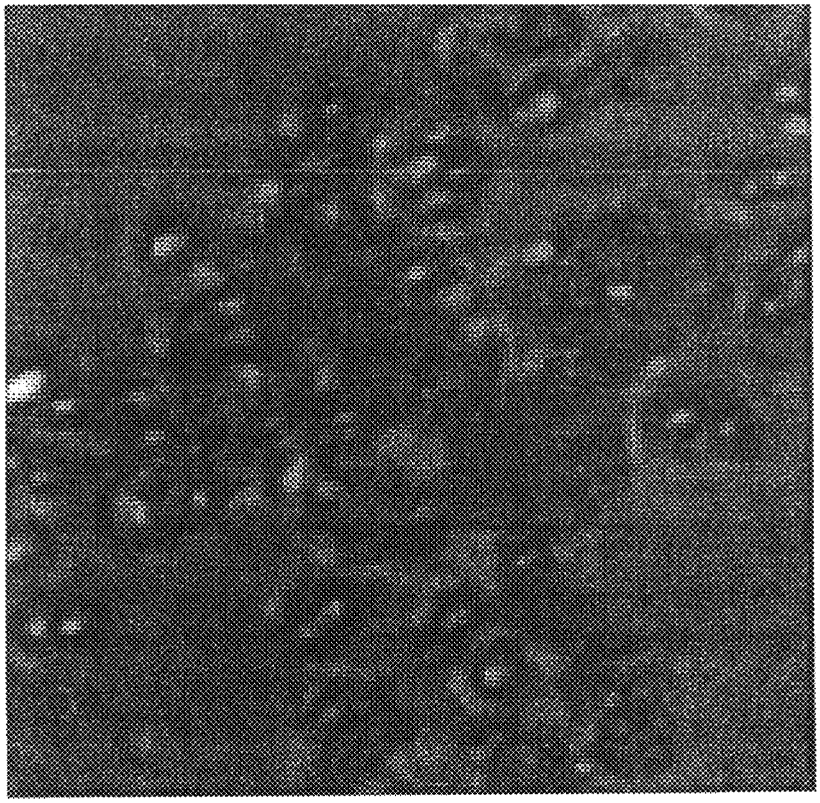
FIGS. 8A, 8B, and 8C are brightfield reflectance, polarized, and color Raman multipoint images, respectively, of a sample of the mixture.
Figure 8B:
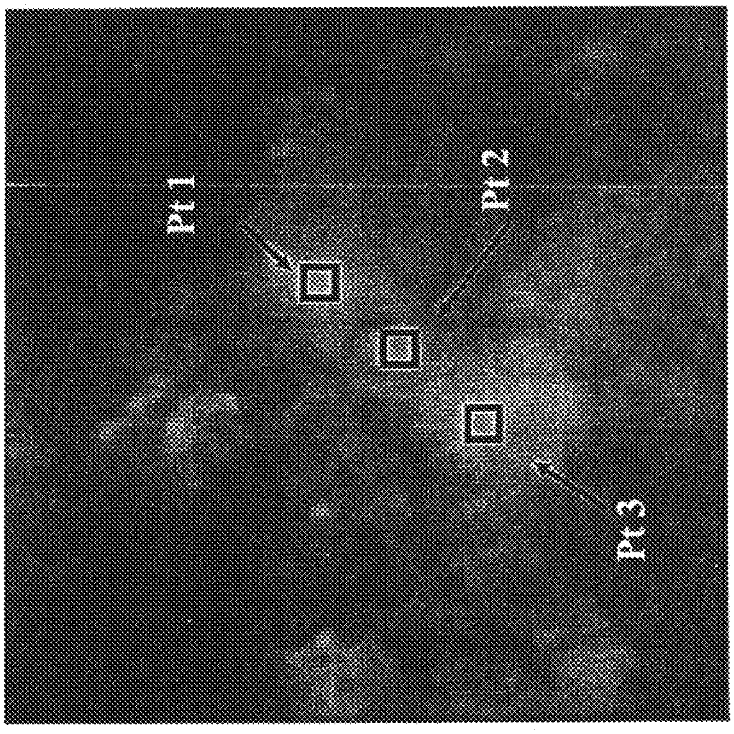
Figure 8C:
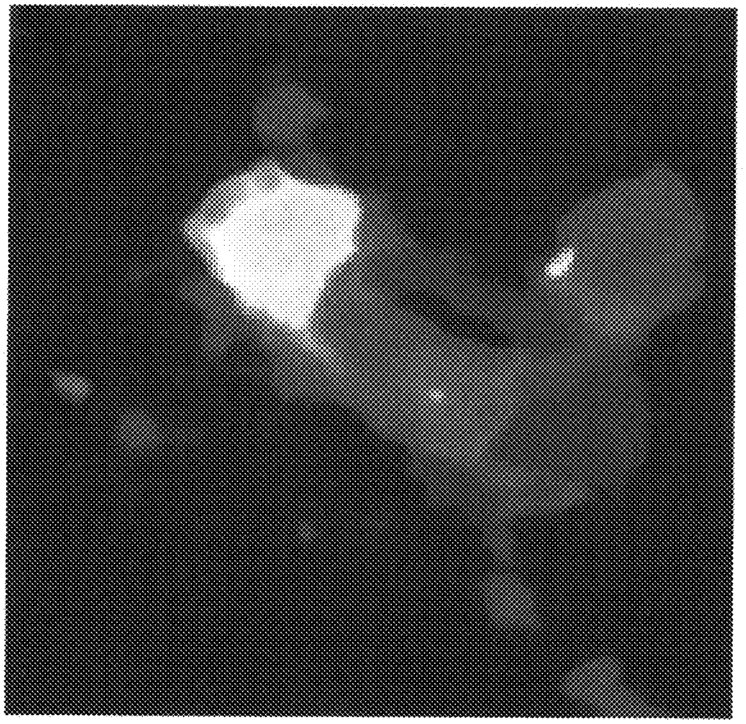
Figure 8D:
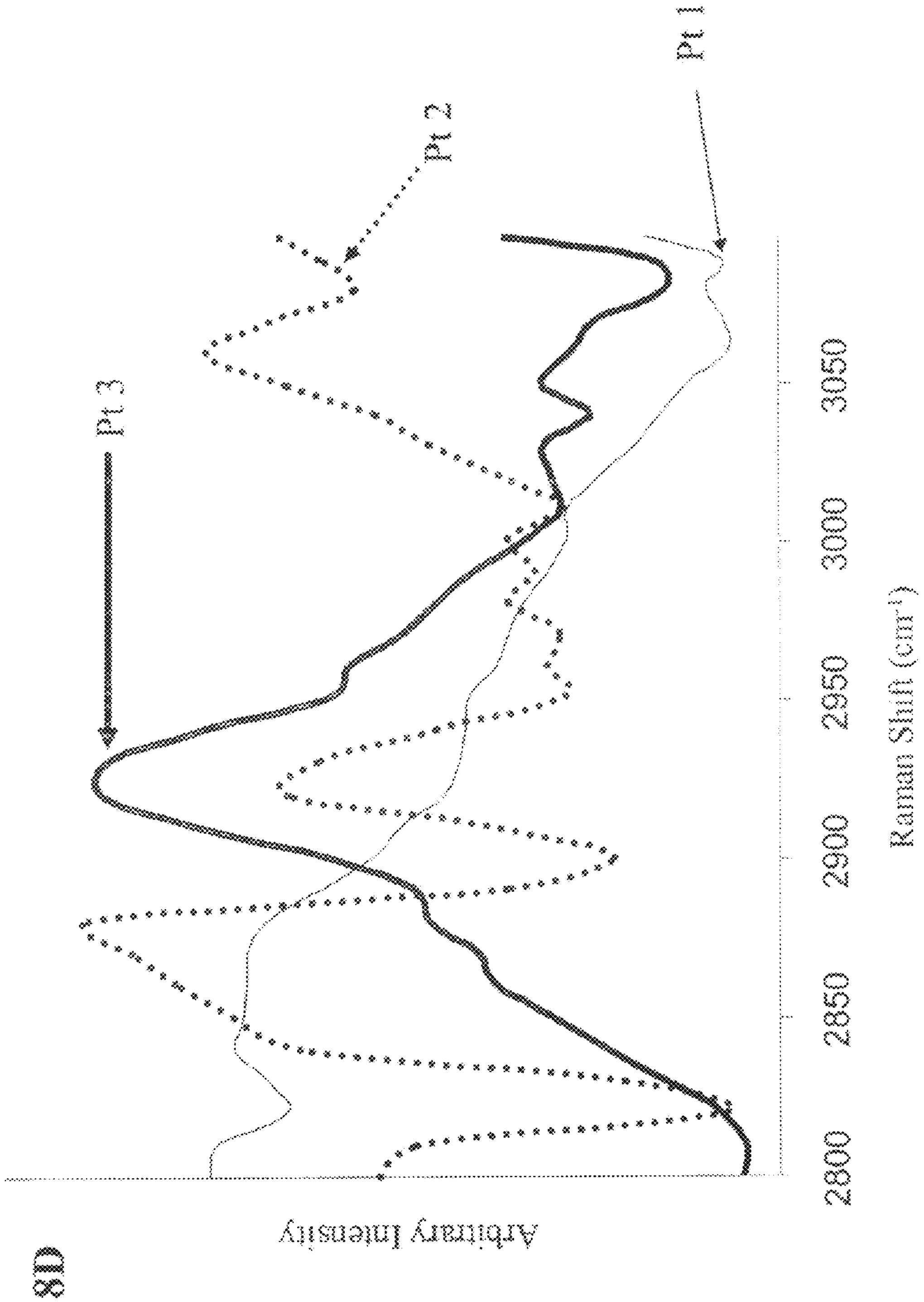
FIG. 8D depicts Raman spectra characteristic of baking soda (Pt1 in FIGS. 8B and 8D), *B. globigii* (Pt2 in FIGS. 8B and 8D), and the sweetener (Pt3 in FIGS. 8B and 8D).
Figure 9A:
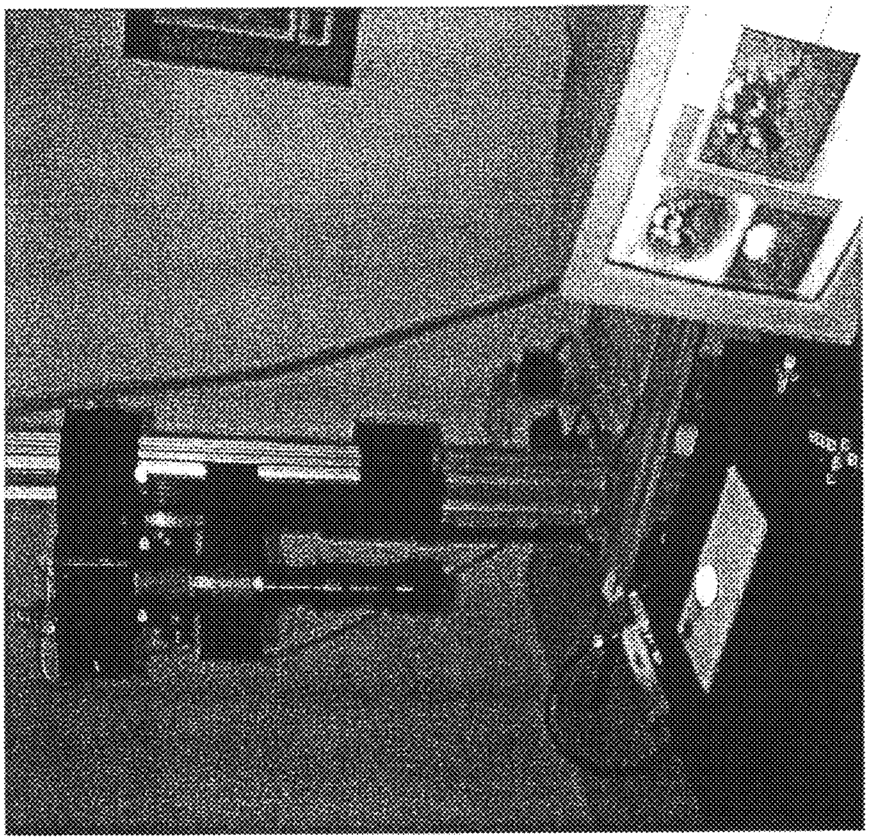
FIG. 9A depicts the configuration of the experiment.
Figure 9B:
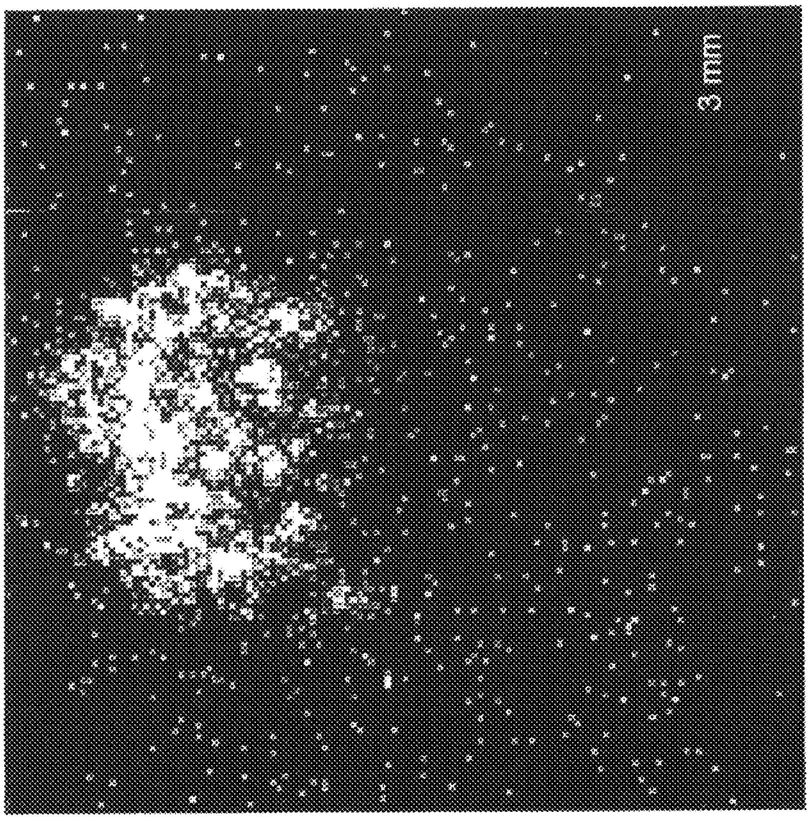
FIG. 9B and color FIG. 9C depict fluorescent images of *B. globigii* spores alone (FIG. 9B) and *B. globigii* mixed with baking soda (FIG. 9C) on an envelope.
Figure 9C:
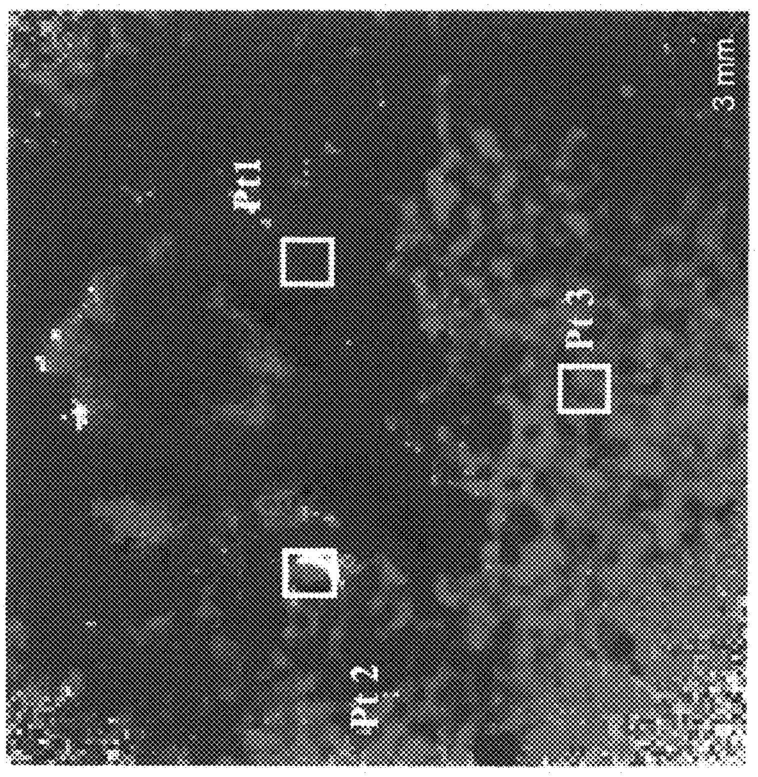
FIG. 9, consisting of FIGS. 9A, 9B, 9C, and 9D, depicts use of fluorescence multipoint sensing performed on a commercial macro platform (CONDOR™ macro imaging system, ChemImage Corp., Pittsburgh, Pa.) for detecting spores of *B. globigii* mixed with baking soda on the exterior of an envelope.
FIG. 9D depicts fluorescent spectral characteristic of baking soda (Pt1 in FIGS. 9C and 9D), *B. globigii* spores (Pt2 in FIGS. 9C and 9D), and the envelope (Pt3 in FIGS. 9C and 9D).
Figure 9D:
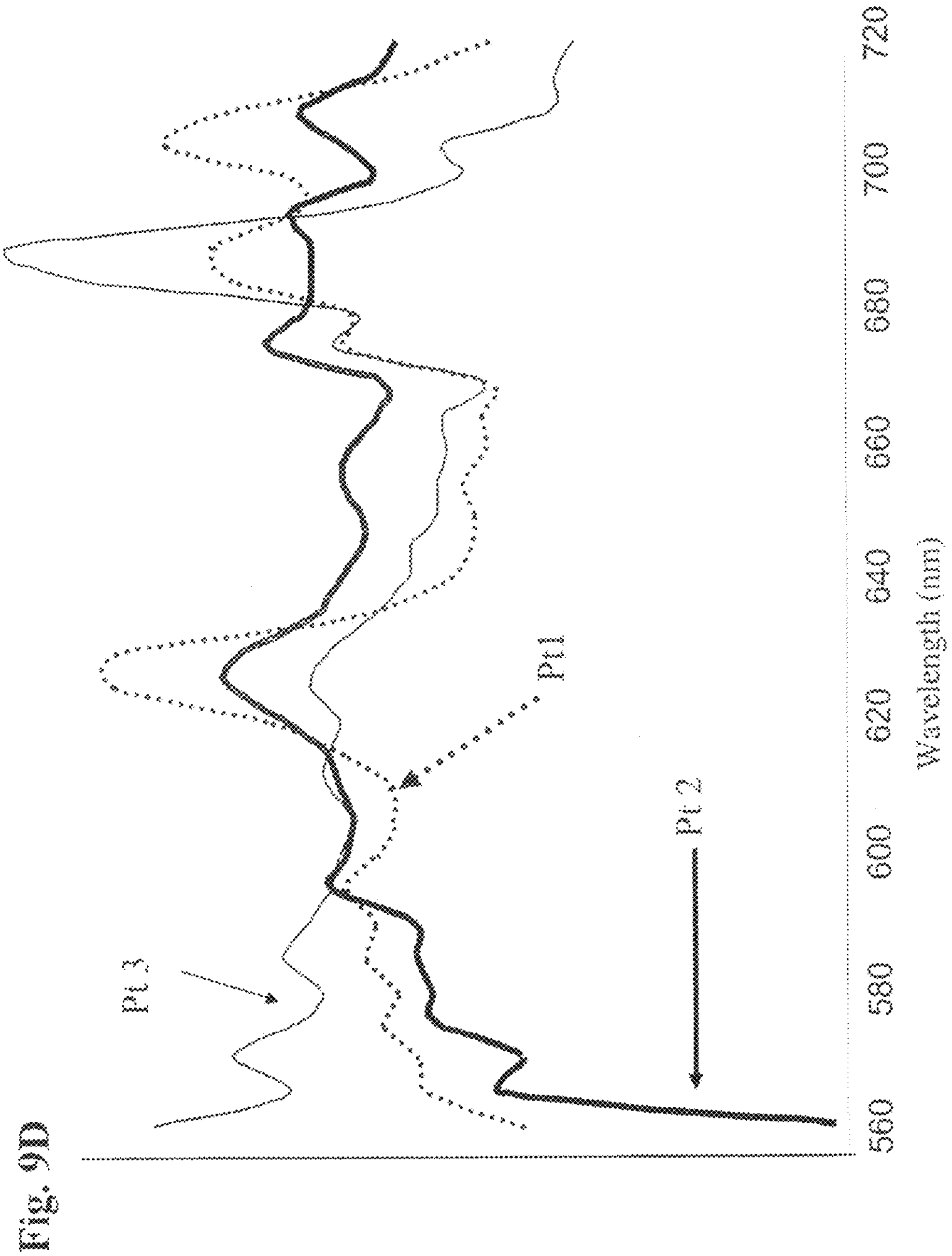
Figure 10A:
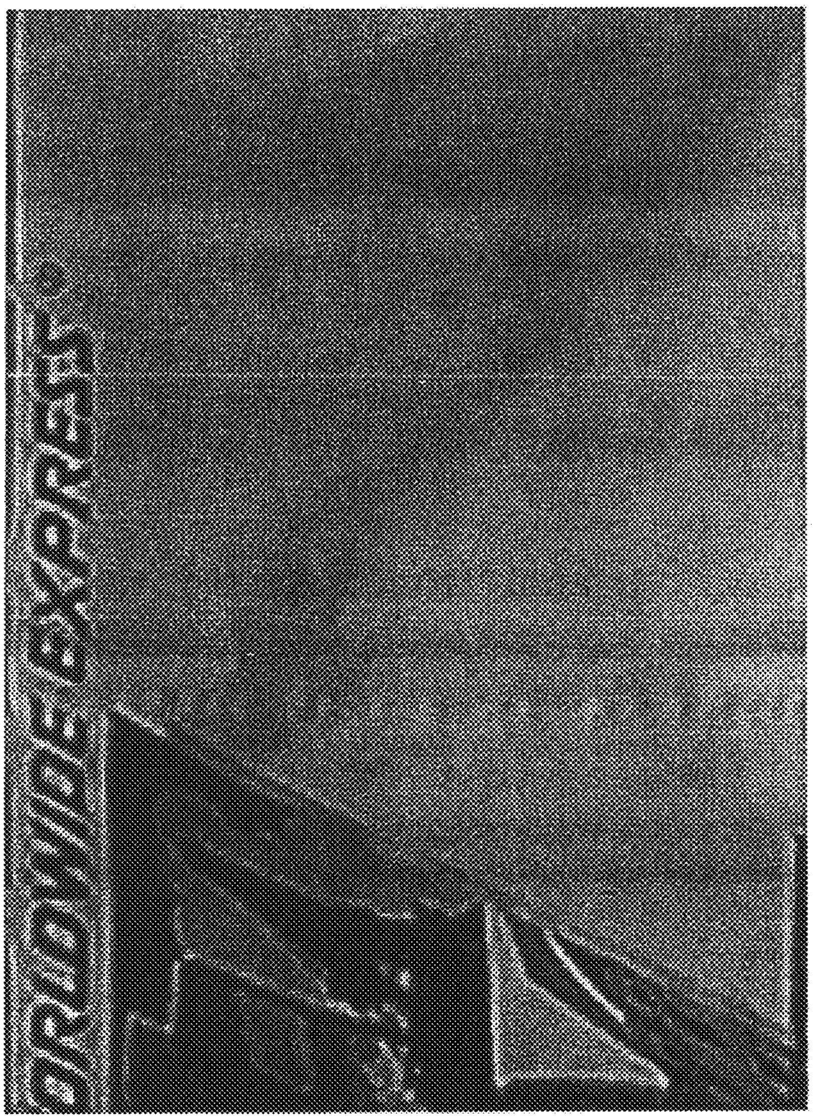
FIGS. 10A and 10B depict visible images combined with NIR images of an empty envelope (FIG. 10A) and an envelope containing objects (FIG. 10B). Color
Figure 10B:
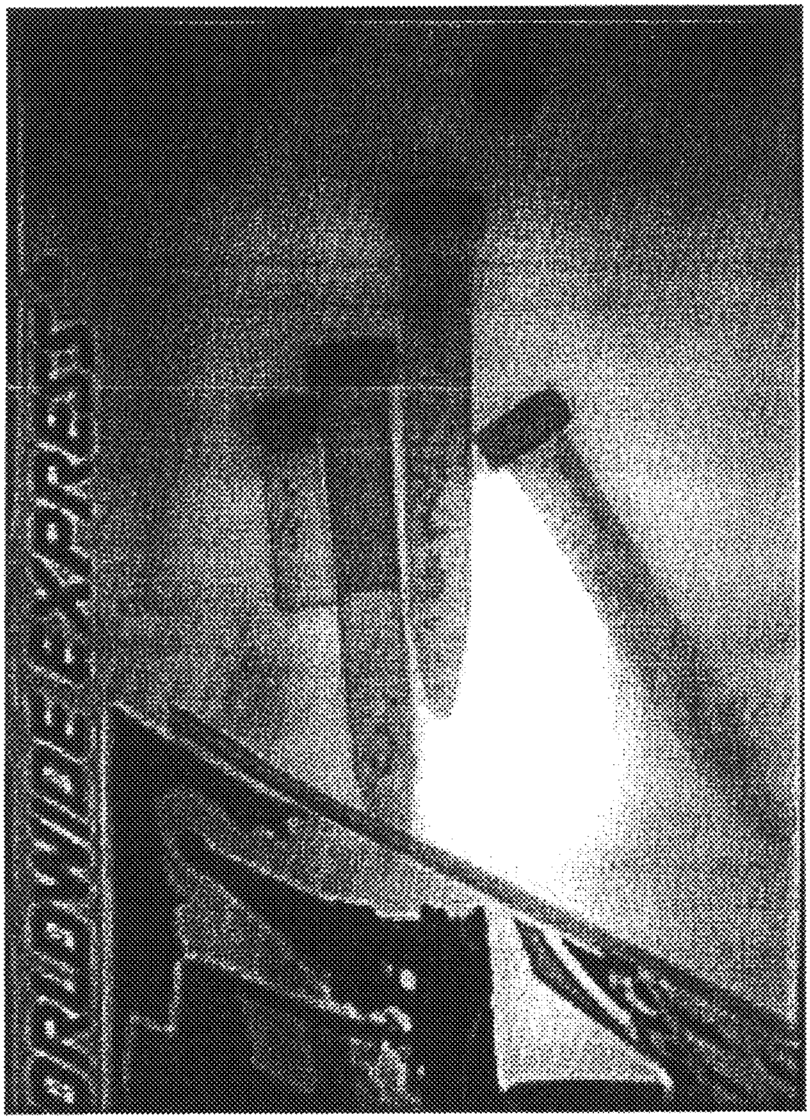
Figure 10C:
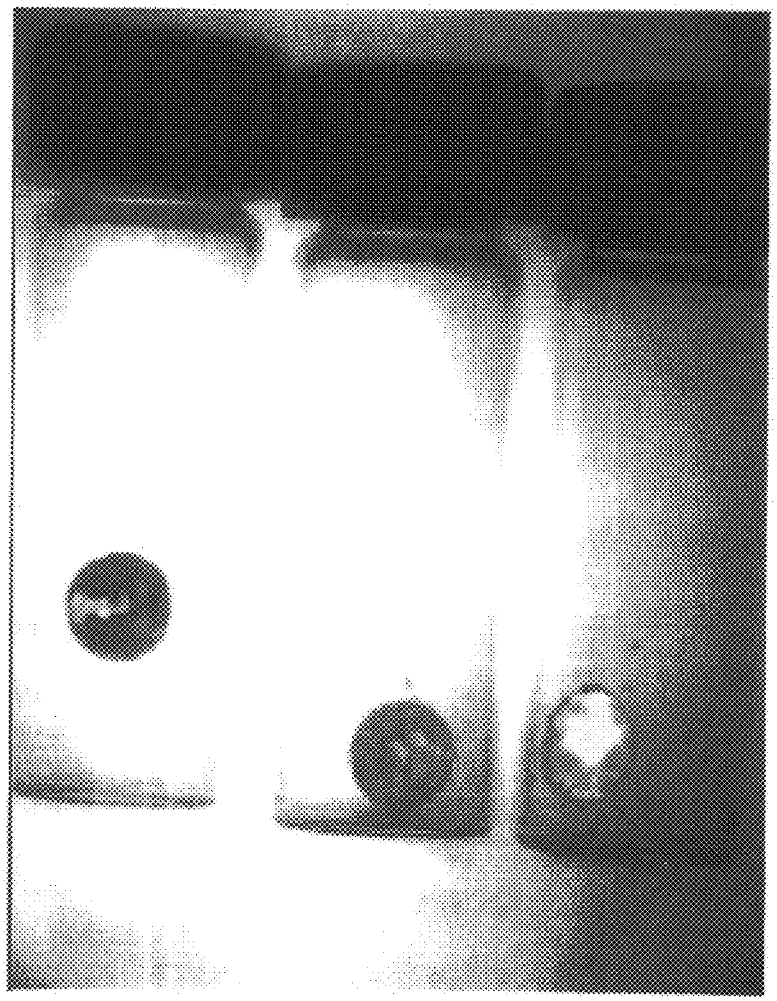
FIGS. 10C and 10D depict the NM images, obtained using the multipoint methods described herein, of envelopes containing lactose, aspirin and *B. thurigiensis* (BT) samples.
Figure 10D:
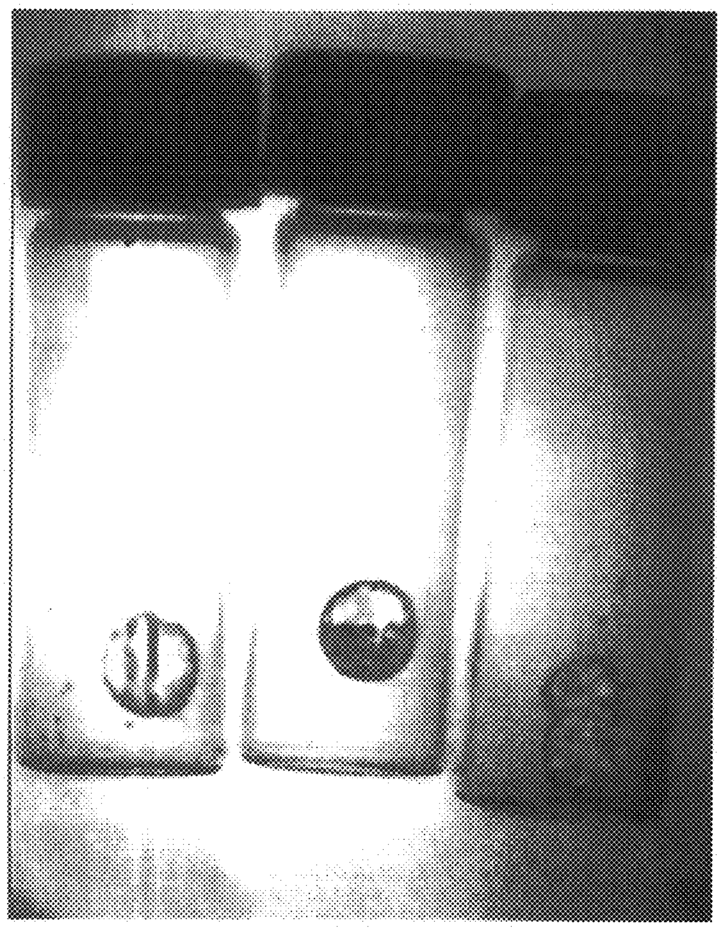

FIG. 7 demonstrates how multipoint spectral sensing and analysis using a fluorescence system can be used to discriminate and distinguish different species of *Bacillus*. The fluorescence spectra in FIG. 7B were obtained from the areas designated "Pt1" and "Pt2," respectively, in FIG. 7A. Based on differences in the fluorescence spectra, particularly at the peak fluorescent emission wavelengths, *Bacillus subtilis* spores (which exhibit a fluorescence peak maximum at 630 nanometers) could be distinguished from *Bacillus pumilus* spores (which exhibit a fluorescence peak maximum at 540 nanometers).

FIG. 8 depicts a Raman multipoint spectral analysis in which *B. globigii* spores were mixed with two powders, baking soda and SWEET-N-LOW® brand saccharine sweetener. FIGS. 8A, 8B, and 8C are brightfield reflectance, polarized light, and Raman spectral images, respectively, of the same field of view of the sample. The Raman spectral features obtained at several areas indicated in FIG. 8B are shown in FIG. 8D and reveal spectral fingerprints that permit identification of the different components by comparison to Raman spectra of the pure components.

FIG. 9 demonstrates that multipoint fluorescence spectral analysis using a macroscope system can be used to detect regions of an envelope at which biotic material resides. The fluorescent spectral analysis can be performed in a multipoint method, and regions which exhibit the presence of biotic material can be subjected to multipoint Raman scattering analysis. In the experiment demonstrated in FIG. 9, *B. globigii* (BG) spores was mixed with a white powder (baking soda) and deposited on the outside of an envelope. Using the system shown in FIG. 9A, fluorescent images of BG spores (FIG. 9B) and the mixture of spores and baking soda (FIG. 9C) were obtained. Fluorescent spectral analysis of points designated "Pt1", "Pt2", and "Pt3" in FIG. 9C are shown in FIG. 9D. The biotic material indicated at Pt2 can be subjected to multipoint Raman spectral analysis (e.g., within the region designated "Pt2" in FIG. 9C and/or the surrounding regions of the envelope), and the biotic material can be more specifically identified, as shown for example in FIG. 4.

FIG. 10 demonstrates that the depth penetration ability of NIR multipoint spectral sensing can be used to detect and identify objects in sealed envelops and containers. FIGS. 10A and 10B shows the visible image of an envelope and the corresponding NIR multipoint identification of objects inside the envelope. FIGS. 10C and 10D show how NIR multipoint spectral sensing discriminates the contents within sealed bottles. Compared to Raman spectroscopy, NIR absorption/reflectance spectroscopy is inherently less selective. Despite this apparent limitation, NIR possesses intrinsic advantages over Raman spectroscopy and Raman chemical imaging in terms of speed and surface area coverage. NIR digital/chemical imaging can be performed in the milliseconds to seconds time range and can be used to visualize microscopic size ranges with submicron spatial resolution to macroscopic size ranges on the order of kilometers.

FIG. 10 demonstrates the ability to detect, visualize and even discriminate various substances enclosed in packaging material using NIR digital/chemical imaging technology despite the commonly-perceived low selectivity associated with the technique. NIR digital imaging enables the detection and visualization of the enclosed vials and contents in real-time. NIR chemical imaging then provides the means by which to classify and discriminate the contents inside the vials. The total acquisition time for the NIR digital/chemical imaging experiment was on the order of a minute. Quicker acquisition times can be achieved by manipulation of imaging parameters and automation in package handling, both of which can be achieved using known methods and merely ordinary, if any, experimentation. FIG. 10 illustrates the sensitivity and speed of NIR absorption/reflectance digital/chemical imaging for the detection, visualization, and classification of biological threat agents enclosed in a sealed container inside packaging material. Although the contents of the shipping package are not apparent in the visible light digital image (FIG. 10A), the NIR digital images reveal the glass and plastic vial forms inside (FIG. 10B). These NIR images were acquired at a frame rate of 30 Hertz. FIGS. 10C and 10D also show the ability to differentiate between materials of similar morphology and color using NIR absorption/reflectance chemical imaging despite the perceived lack of specificity associated with the technique. The NIR digital/chemical overlay images in FIGS. 10C and 10D reveal the structure of three glass vials and discriminate their contents—lactose, aspirin, and BT. These results demonstrate that NIR can be used to discriminate materials such as these. Raman spectroscopic examination of the materials can rapidly confirm the identity of the materials.

A wide variety of biological pathogens can be detected using the multipoint spectral sensing methods described herein (i.e., for detection, classification as to species or strain, determination of viability, or some combination of these). These include eukaryotes such as protozoans and fungi (e.g., *Giardia* species, *Candida albicans*, or *Cryptosporidium* species in water or soil); bacteria (e.g., *Escherichia coli, Yersinia pestis, Francisella tularensis, Brucella* species, *Clostridium perfringens* and other species of Clostridia, *Burkholderia mallei, Burkholderia pseudomallei, Chlamydia psittaci, Coxiella burnetii, Rickettsia prowazekii, Vibrio* species, *Enterococcus faecalis, Staphylococcus epidermidis, Staphylococcus aureus, Enterobacter aerogenes, Corynebacterium diphtheriae, Pseudomonas aeruginosa, Acinetobacter calcoaceticus, Klebsiella pneumoniae, Serratia marcescens*); and viruses (variola, vaccinia, filoviruses such as Ebola and Marburg viruses, naviruses (such as Lassa fever and Machupb viruses), and alphaviruses (such as Venezuelan equine encephalitis, eastern equine encephalitis, and western equine encephalitis viruses). The methods can also be used to detect the causative agents of any viral, bacterial, parasitic, or prion disorder, including for example causative agents of disorders such as tularemia, brucellosis, glanders, melioidosis, psittacosis, Q fever, typhus, smallpox, and encephalitis.

In addition, just as toxic components in a masking mixture can be detected, so can specific materials in other mixtures be similarly determined. These includes but is not limited to a wide range of mixtures such as hazardous agents in blood, impurities or active ingredients in drug tablets, and specific entities among airborne particulates.

Data Analysis

Data analysis and chemometric tools examine the differences in fluorescence or Raman spectra found for each of the multipoint spectra and perform a separation into principle components to distinguish the pure components and identify the respective component, for example by comparison with a reference database of spectra stored in data storage entity 430 of FIG. 1. Methods of comparing a Raman spectrum with one or more reference spectra are known in the art.

A variety of data processing procedures can be used with these systems. For example, a weighted multi-point spectral data subtraction routine can be used to suppress contribution from the sample background or sample support (e.g., Raman light scattered by a microscope slide). Alternatively, multivariate spectral analysis involving principal factor analysis and subsequent factor rotation can be used for differentiation of pure molecular features in hazardous agents and other entities (e.g., non-threatening 'masking' compounds).

The following is an example of an algorithm that can be used to perform this multi-point analysis of fluorescence spectra collected for a mixture of *Bacillus subtilis* and *B. pumilus* spores as a sample:

1. Divide the raw multipoint data set (mp-data set) by a background mp-data set (taken without the sample).

2. Apply cosmic event filtering on the resultant mp-data set (median filtering for points whose value differs significantly from the mean of a local neighborhood).

3. Use an alignment procedure to correct for any slight movements of the sample during data collection.

4. Apply a spatial average filter.

5. Perform a spectral normalization (helps correct for varying illumination across the sample).

6. Perform a spectral running average over each set of three spectral values.

7. Extract a set of frames corresponding to 550 to 620 nanometers. The spectra for both bacterial spores (*B. subtilis* var *niger* and *B. pumilus*) can be essentially linear over this range. For example, *B. subtilis* var *niger* can have a positive slope and *B. pumilus* can have a negative slope.

8. Create a single frame mp-data set in which each intensity value is the slope of the spectral sub-region (from the last image). The slope is determined via a least-squares fit.

9. Scale the resulting mp-data set between 0 and 4095. Keep track of the point from 0 to 4095 that corresponds to 0 in the prior image (the "Zero point").

10. Create a mask mp-data set image from a series of steps:

10a. From the aligned image (step 3), calculate a single frame "brightest" mp-data set in which the intensity of each point is the maximum intensity value for each spectrum.

10b. Scale this brightest mp image set between 0 and 4095.

10c. Create a binarized mp data set from the scaled mp data set, in which every point whose intensity is greater than 900 is set to 1 in the new mp data set and every point whose intensity is less than 900 is set to 0 in the new mp-data set. The value of 900 was chosen by an examination of the histogram associated with the scaled mp data set. (An improvement to this algorithm is to automatically select the threshold by numerically analyzing the histogram for a given mp data set.)

11. Multiply the scaled mp-data set from step 9 by the mask mp data set from step 10. The result is a gray scale mp data set in which intensity values below the zero value defined in step 9 correspond to *B. pumilus* and the intensity values above the zero point correspond to *B. subtilis* var *niger*.

12. The final RGB mp data set is then created by setting all the "negative" values to red and all the "positive" values to green.

Applications

The devices, systems, and methods described herein are suitable for rapid hazardous agent detection and other applications. Configured in a macroscope version as described herein, multipoint spectroscopic sensing can be employed for rapid assessment of large areas for suspected hazardous agents based on their fluorescence, NIR properties, UV/visible properties, or some combination of these. Configured in a microscope-based version, visualization, positive detection, classification, and identification of suspected hazardous agents can be made. Configured in the endoscopic mode, hazardous agents can be visualized, detected, classified, and identified remotely. Configured in FAST mode, hazardous agents can be detected, classified, identified, and visualized remotely or at the microscope in real-time. When configured as an air sampler, unambiguous detection of hazardous agents aerosols can be performed.

Advantages Over Currently Available Technology

Traditional approaches to detection of hazardous biological agents include inoculation methods, enzyme-linked immunosorbent assay (ELISA) methods, BIOTHREAT ALERT™ (Tetracore Inc, Gaithersburg, Md.; BTA) test strips, DNA-based tests, DNA chip analyses, and mass spectrometry.

Inoculation methods involve the inoculation of suspect culture or specimen into an animal that is then observed for development of disease. In addition to animal cruelty issues, drawbacks of this approach include the extensive amount of time required to achieve detection.

ELISA tests involve antibody detection. This technique is also slow and suffers from a high rate of false positive results (e.g., unrelated antibody reacts with antigen nonspecifically) and false negative results (e.g., interfering compounds present in blood or antibodies not concentrated enough to be detected). Furthermore, a patient can test positive to antibodies long after the patient has recovered.

BTA test strips are small plastic devices that work very much like a home pregnancy test. The test strips contain specific antibodies that change color on the strip indicating the presence of a bio-threat agent. A negative result means the bio-threat agent is not present within the detection limit of the strip. Although results can be obtained in a relatively short period (e.g., 15 minutes), the incidence of false negatives and false positives is high.

DNA-based tests detect agents by recognizing their genetic sequences. While more sensitive than BTA test strips, DNA-based tests are susceptible to masking agents and involve a lengthy analysis time. DNA chip analysis involves the immobilization of DNA strands on a Si or glass wafer chip. DNA will bind to or hybridize complementary DNA strands in the sample being tested. A specially designed microscope detects DNA hybridization. Amplification is achieved by polymerase'chain reaction (PCR). Detection of bio-threat agent is reported to be possible within minutes.

The limitations of DNA-based methods are two-fold. First, DNA methods are designed to detect a specific bio-threat agent by virtue of its unique DNA sequences. Therefore, each DNA test is specific to one agent and if it is desired to detect additional agents, additional test reagents must be developed. A second limitation involves the problems of false negatives and false positives due to environmental contamination. DNA tests are well known to have problems yielding correct results in "real-world" samples.

Mass Spectrometry (MS) uses the pattern of mass fragments generated when a cell, spore, or chemical is subjected to an ionization process under high vacuum to characterize the organism(s) or chemical(s) present in a sample. This technique has the advantage of very sensitive detection, but requires a sophisticated sampling system in order to deliver a representative sample to the ionizer. The main limitation of MS is that it requires the use of high vacuum pumps that are inherently delicate and expensive. An additional limitation is that it is a destructive technique.

Alternative embodiments of the devices and systems described herein include probes or microscopes based on spectroscopic methods including Raman, fluorescence, NIR, and others for rapid, non-contact, and accurate detection of BWAs and CWAs. These techniques have been previously applied in a time consuming approach involving spectroscopically addressing one single specific point at a time. The multipoint spectral sensing method described herein rapidly provides data needed for automated spectral analytical methods. Partial component analysis approaches can be used in combination with these methods for chemical imaging analysis. The multipoint spectral sensing methodology described herein can be implemented in a miniaturized, compact sensing platform. The devices, systems, and methods described herein can be used to identify the distribution of individual hazardous agents in the presence of other hazardous agents, environmental contaminants, and/or non-threatening 'masking' agents in either local or remote environments. These are characteristics that no traditional method provides. The devices, systems, and methods described herein can exhibit a lower incidence of false positive and false negatives results and permit one to determine if a true bio-threat exists in a time frame of seconds to minutes.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

The invention claimed is:

1. A method of assessing the occurrence of a hazardous agent in a sample located in a field of view, the method comprising:

irradiating said sample to thereby generate a first plurality of interacted photons from a first set of multiple points in the sample, wherein said first plurality of interacted photons are selected from the group consisting of: photons absorbed by said multiple points, photons reflected by said multiple points, photons emitted by said multiple points, and combinations thereof, and wherein said first set of multiple points represent a portion of total points in the field of view;

assessing said first plurality of interacted photons to thereby generate a first spectroscopic data set representative of said sample; and analyzing said first spectroscopic data set to thereby determine at least one of: the presence of a hazardous agent in said sample and the absence of a hazardous agent in said sample.

2. The method of claim 1 wherein said first plurality of interacted photons are assessed using at least one of: infrared spectroscopy, fluorescence spectroscopy, UV/visible spectroscopy, and combinations thereof.

3. The method of claim 1 wherein said hazardous agent comprises at least one chemical agent.

4. The method of claim 1 wherein said hazardous agent comprises at least one biological agent.

5. The method of claim 1 wherein said hazardous agent comprises at least one microorganism.

6. The method of claim 1 wherein said hazardous agent comprises at least one bacterium.

7. The method of claim 1 wherein said hazardous agent comprises at least one protozoan.

8. The method of claim 1 wherein said hazardous agent comprises at least one virus.

9. The method of claim 1 further comprising passing said first plurality of interacted photons through a filter.

10. The method of claim 9 wherein said filter is selected from the group consisting of: Fabry Perot angle tuned filter, an acousto-optic tunable filter, a liquid crystal tunable filter, a Lyot filter, an Evans split element liquid crystal tunable filter, a Solc Liquid crystal tunable filter, and a liquid crystal Fabry Perot tunable filter, and combinations thereof.

11. The method of claim 1 further comprising passing said first plurality of interacted photons through an interferometer.

12. The method of claim 11 wherein said interferometer is selected from the group consisting of: a polarization-independent imaging interferometer, a Michelson interferometer, a Sagnac interferometer, a Twynam-Green interferometer, a Mach-Zehnder interferometer, and a tunable Fabry Perot interferometer, and combinations thereof.

13. The method of claim 1 further comprising passing said first plurality of interacted photons through a dispersive spectrometer.

14. The method of claim 1 wherein said first plurality of interacted photons are collected using a device selected from the group consisting of: a telescope, a macroscope, a microscope, an endoscope, a fiber optic array, and combinations thereof.

15. The method of claim 1 wherein said first set of multiple points have a defined geometric relationship.

16. The method of claim 15 wherein the geometric relationship of said first set of multiple points is defined based on a spectroscopic feature of the sample.

17. The method of claim 1 wherein interacted photons from at least three points is assessed.

18. The method of claim 1 wherein interacted photons from at least five points is assessed.

19. The method of claim 1 wherein the interacted photons from at least ten points is assessed.

20. The method of claim 1 wherein the interacted photons from at least fifty points is assessed.

21. The method of claim 1 further comprising:

illuminating said sample to thereby generate a second plurality of interacted photons from a second set of multiple points, wherein said second plurality of interacted photons is selected from the group consisting of: photons absorbed by said sample, photons reflected by said sample, photons emitted by said sample, and combinations thereof, and wherein said second set of multiple points corresponds to at least one point in said first set of multiple points wherein said hazardous agent was detected; and assessing said second plurality of interacted photons to thereby determine at least one of: the presence of a hazardous agent and the absence of a hazardous agent.

22. The method of claim 1 wherein said analyzing comprises comparing said first spectroscopic data set to at least one reference data set corresponding to a known hazardous agent.

23. The method of claim 1 wherein at least three of the multiple points are collinear.

24. The method of claim 1 wherein at least three of the multiple points are colinear along a first line and wherein another at least three of the multiple points are colinear along a second line.

25. The method of claim 1 wherein at least four of the multiple points are radially equidistant from a central point.

26. The method of claim 1 wherein the field of view is in a microscopic field with the sample in the microscopic field, and the multiple points represent not more than 25% of the area of the microscopic field.

27. The method of claim 1 wherein the field of view is in a microscopic field with the sample in the microscopic field, and the multiple points represent not more than 5% of the area of the microscopic field.

28. The method of claim 1 wherein the field of view is in a microscopic field with the sample in the microscopic field, and the multiple points represent not more than 1% of the area of the microscopic field.

29. The method of claim 21 further comprising:

illuminating said sample to thereby generate a third plurality of interacted photons from a third set of multiple points, wherein said third plurality of interacted photons is selected from the group consisting of: photons absorbed by said sample, photons reflected by said sample, photons emitted by said sample, and combinations thereof, and wherein said third set of multiple points corresponds to at least one point in said second set of multiple points wherein said hazardous agent was detected; and assessing said third plurality of interacted photons to thereby determine at least one of: the presence of a hazardous agent and the absence of a hazardous agent.

30. A device for assessing the occurrence of a hazardous agent in a sample, the device comprising:

a radiation source for irradiating said sample;

a detector for simultaneously detecting a first plurality of interacted photons from multiple discrete portions of said sample; and a controller operably linked to said detector for restricting detection of said first plurality of interacted photons to the multiple discrete portions of said sample.

31. The device of claim 30 further comprising a tunable filter.

32. The device of claim 30 wherein said detector is selected from the group consisting of: an infrared detector, a fluorescence detector, a UV/visible detector, and combinations thereof.

* * * * *